United States Patent
Lodha et al.

(10) Patent No.: US 11,232,663 B2
(45) Date of Patent: Jan. 25, 2022

(54) SYSTEM AND METHOD USING OPTICAL TAGS TO CONDUCT SECURE TRANSACTIONS AND AUTHENTICATIONS

(71) Applicants: Lalit Lodha, Boston, MA (US); Joshua Huntington, Chandler, AZ (US)

(72) Inventors: Lalit Lodha, Boston, MA (US); Joshua Huntington, Chandler, AZ (US)

( * ) Notice: Subject to any disclaimer, the term of this patent is extended or adjusted under 35 U.S.C. 154(b) by 73 days.

(21) Appl. No.: 16/870,979

(22) Filed: May 10, 2020

(65) Prior Publication Data

US 2021/0350648 A1   Nov. 11, 2021

(51) Int. Cl.
| | |
|---|---|
| G07C 9/27 | (2020.01) |
| G16H 10/40 | (2018.01) |
| A61B 5/1171 | (2016.01) |
| A61B 5/1172 | (2016.01) |
| G06F 21/32 | (2013.01) |
| A61B 5/117 | (2016.01) |
| G06K 9/00 | (2006.01) |
| G07C 9/25 | (2020.01) |
| G06Q 20/40 | (2012.01) |

(52) U.S. Cl.
CPC ....... *G07C 9/257* (2020.01); *G06Q 20/40145* (2013.01); *G07C 9/27* (2020.01)

(58) Field of Classification Search
CPC .................................................... G07C 9/257
See application file for complete search history.

(56) References Cited

U.S. PATENT DOCUMENTS

| | | | | |
|---|---|---|---|---|
| 7,908,155 B2* | 3/2011 | Fuerst | ............ | G16H 10/20 |
| | | | | 705/3 |
| 9,805,213 B1* | 10/2017 | Kragh | ............ | H04L 63/0861 |
| 10,923,216 B1* | 2/2021 | White | ............ | G06F 16/2365 |
| 2008/0091471 A1* | 4/2008 | Michon | ............ | G16H 50/70 |
| | | | | 705/3 |

* cited by examiner

*Primary Examiner* — Mohamed Barakat
*Assistant Examiner* — Pameshanand Mahase
(74) *Attorney, Agent, or Firm* — Handal and Morofsky LLC; Anthony H. Handal

(57) ABSTRACT

A method for limiting exposure to infectious disease by controlling access to a controlled access venue to admit individuals who have tested non-infectious for a particular highly infectious disease or have received a vaccination against the same comprises receiving, at a central website operator server, consumer user identification information from consumer users and storing that information in a consumer user database associated with the server. A biometric identifier from the consumer users is transmitted to the consumer user database and each associated with its respective associated consumer user to form an enrollment record. Identity of a presented individual is collected at a medical certification point and an authority record is created in an accessible authority database. At said medical certification point, an antibody test or vaccination is administered and the same is noted in the authority record. A biometric is collected from a venue presented consumer at a presentation venue, compared to authority records for a match, and the result provided to the venue.

15 Claims, 25 Drawing Sheets

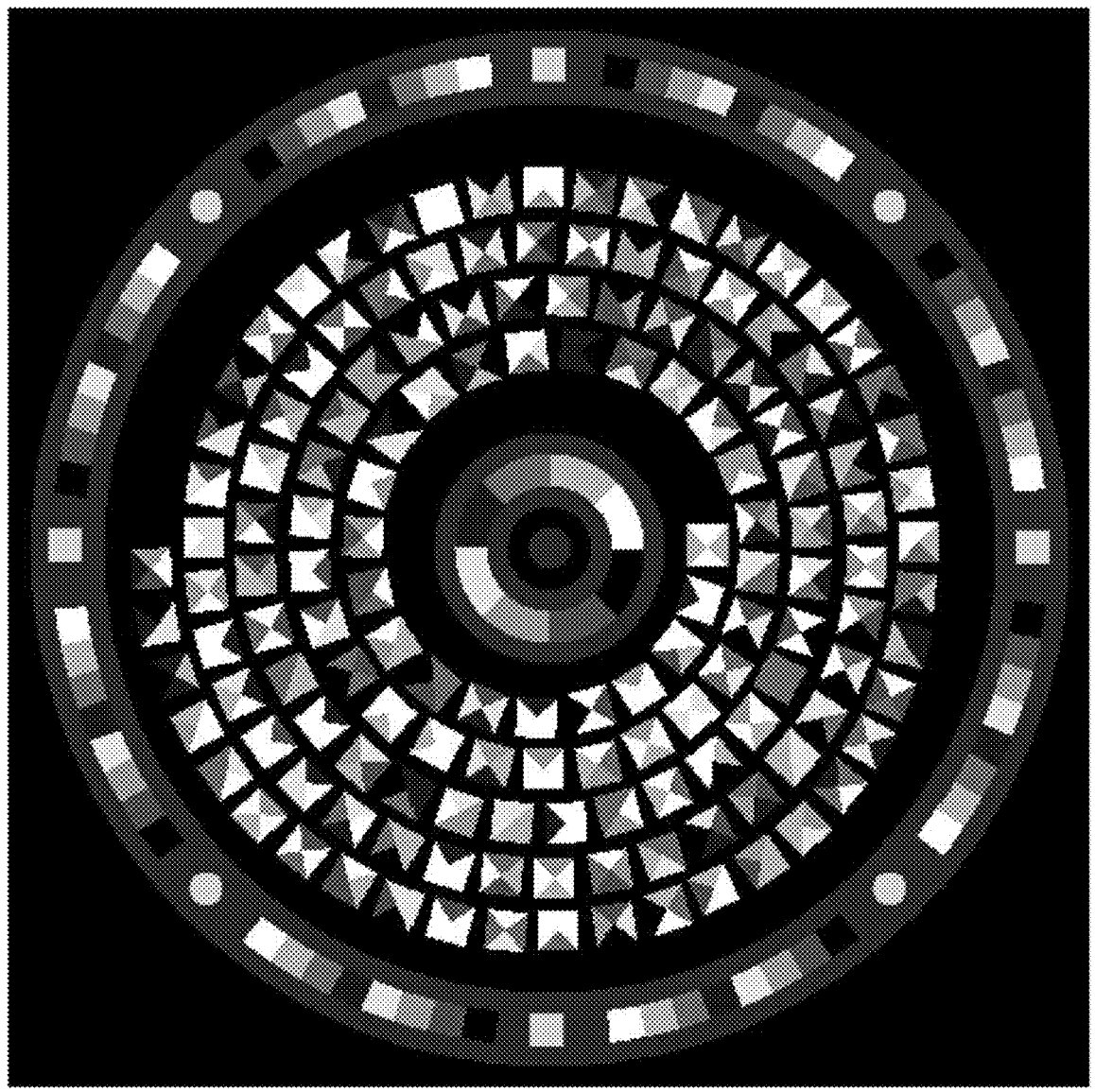
Fig. 1 Example of Mosaic
A Mosaic can vary in size

Fig. 2 Another example of Mosaic
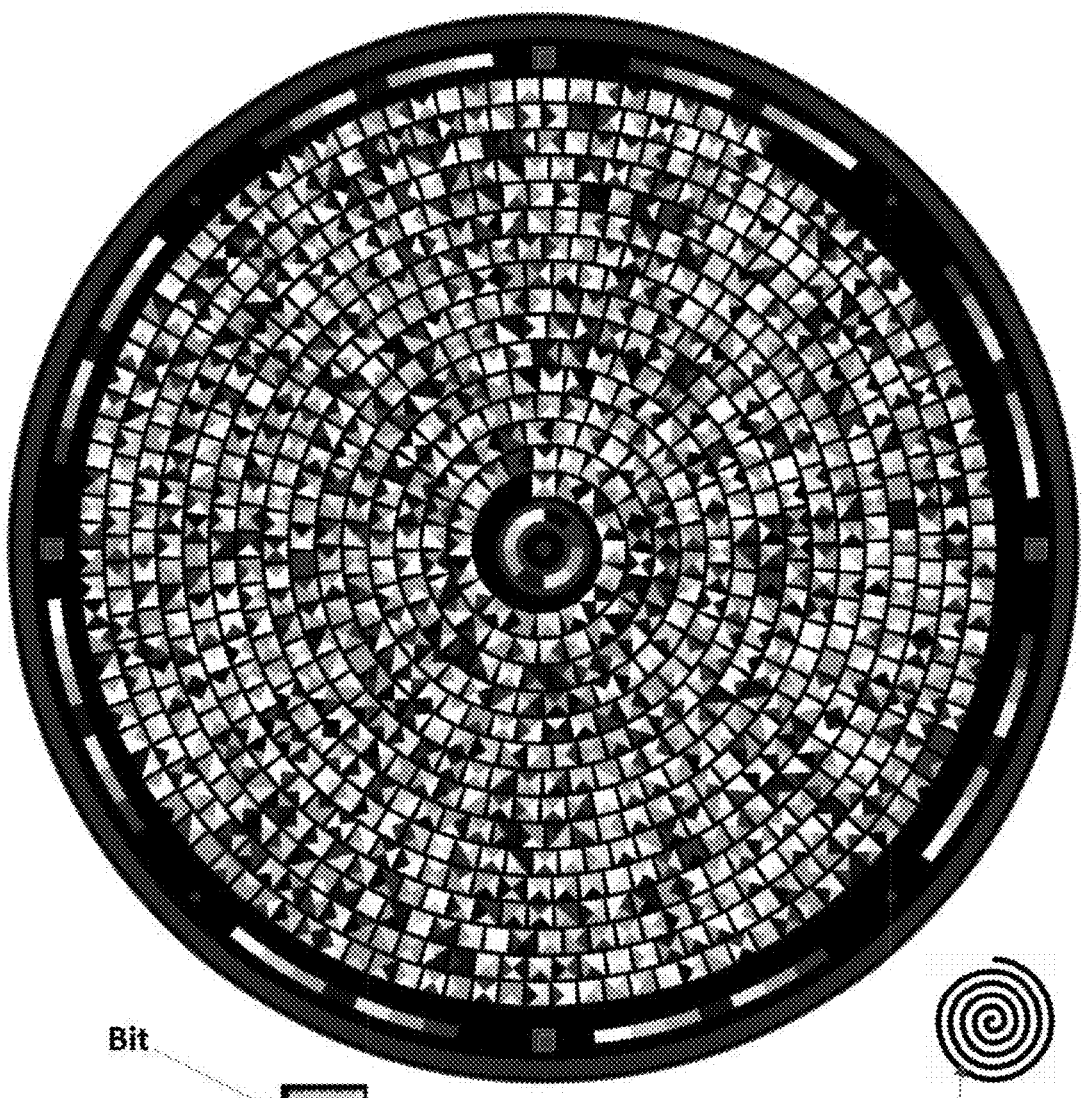
Bit
Fig 2.a. Mosaic is comprised of Bits (square as shown but can be any symbol, shape, picture or animation).
Fig 2.c. Bits are winding outward in a circular pattern. These Bits may go outward to the and turn around to come back in, then return out again till the pattern is complete.

Fig. 3 CLAIM #1 and 9 include but not limited to the following:
SHAPES OF MOSAIC – EXAMPLE
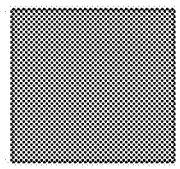 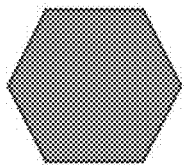 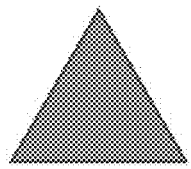 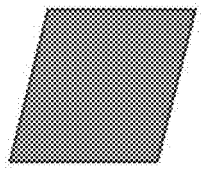
4 SIDED    HEXAGON    3 SIDED    4 SIDED PARALLELAGRAM
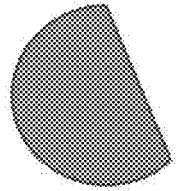
PART CIRCULAR SHAPE

FLOW OF BITS

SPIRAL

VARIOUS PATHS

PATH BASED

Fig. 7 Another example of Mosaic
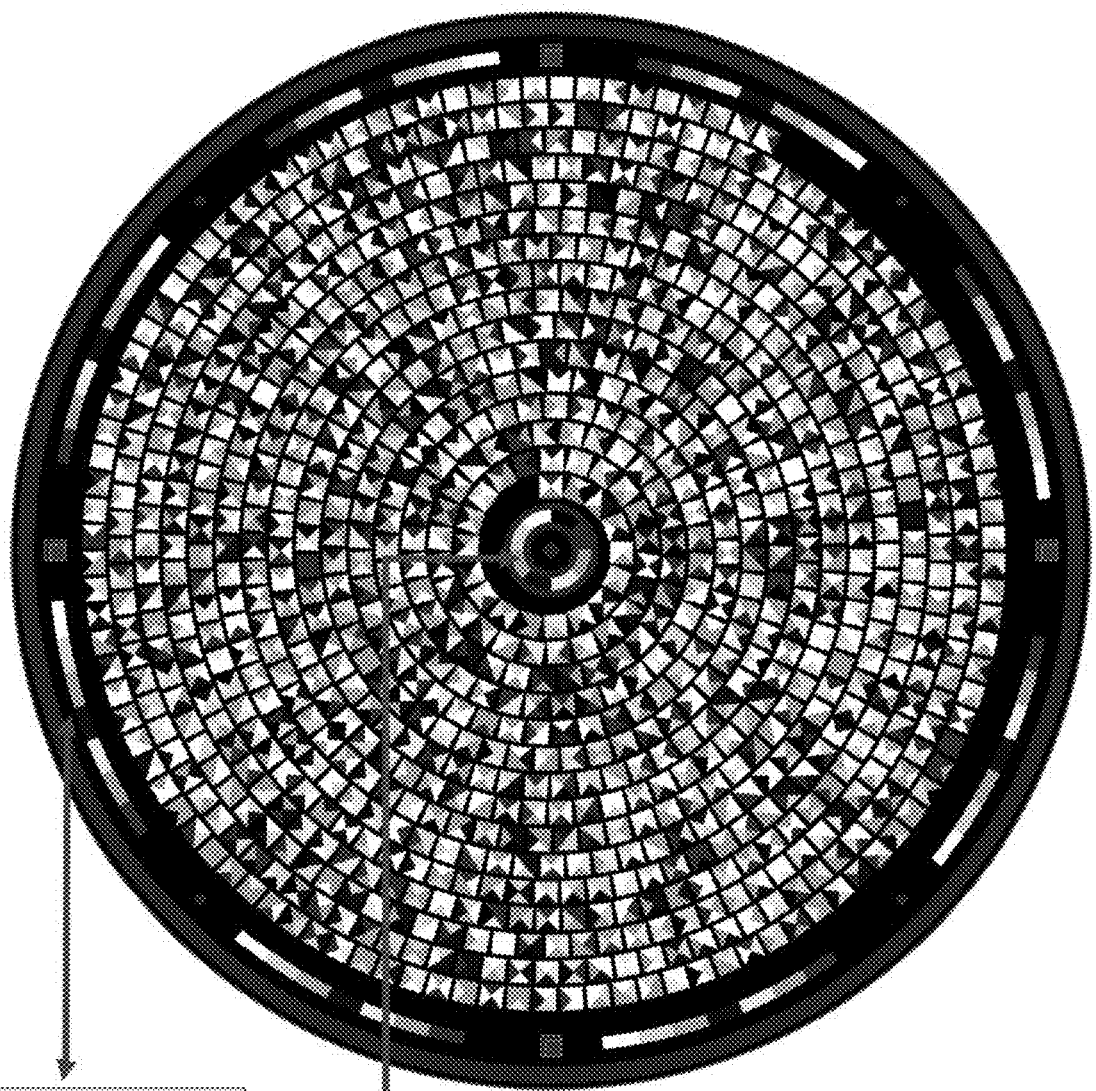
7. A color pallet is shown in the center of the Mosaic and a series of color pallets are shown at the edge of the Mosaic

Fig. 8 CLAIM #9 EXAMPLE OF BIT TYPES: ANY SHAPE, SYMBOL, PICTURE, ANIMATION
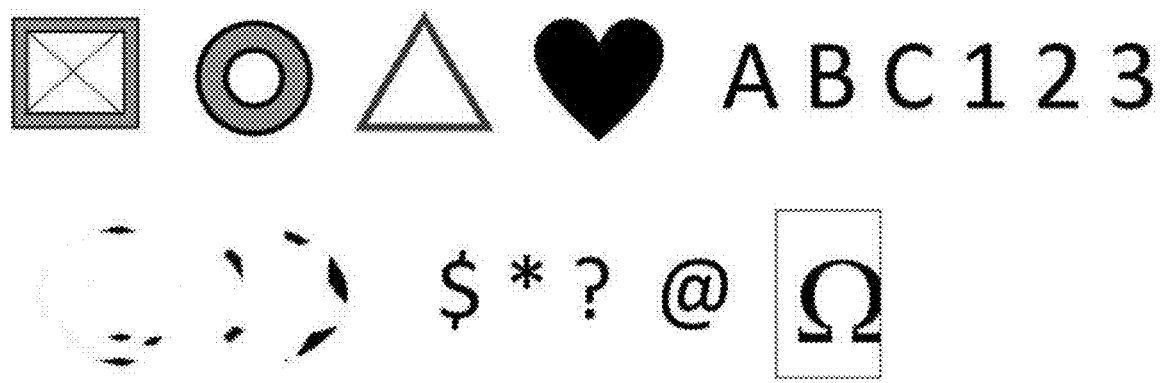
Fig. 9
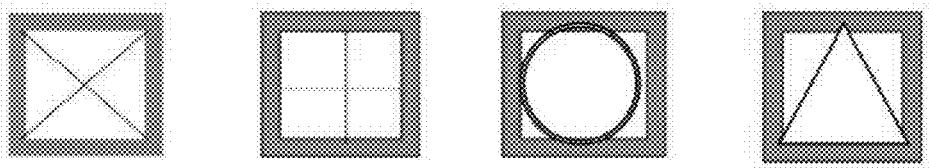
Fig. 10
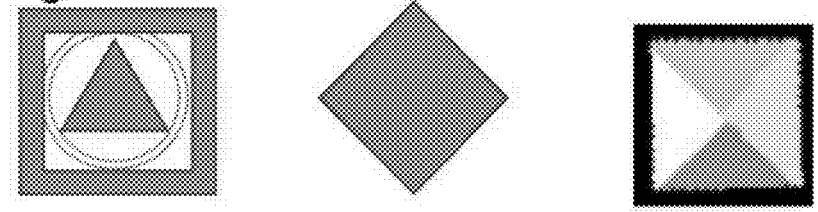

Fig. 11 CLAIM 15

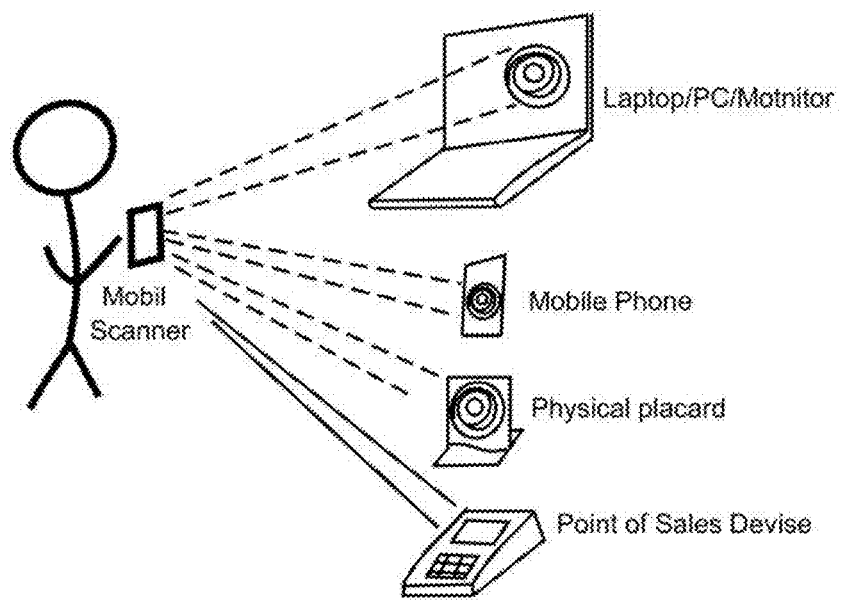
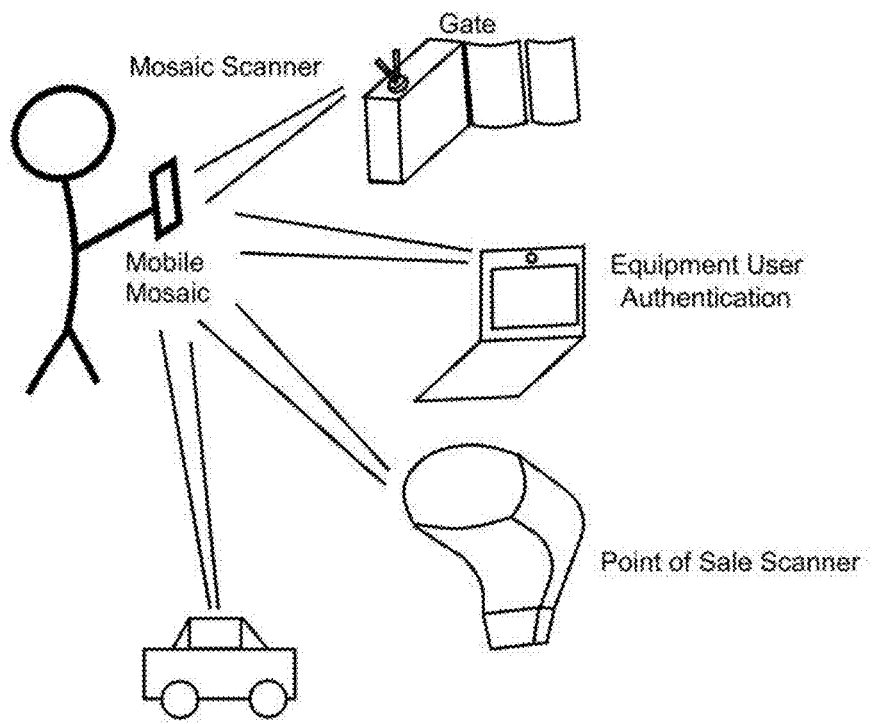
Fig. 12

Claim 150 Methodology

Claim 160 Methodology  Fig. 15

Claim 170 Methodology   Fig. 16

SYSTEM AND METHOD USING OPTICAL TAGS TO CONDUCT SECURE TRANSACTIONS AND AUTHENTICATIONS

TECHNICAL FIELD

The invention relates to apparatus and methods for securely conducting brick and mortar commerce, e-commerce and authentications using a mobile device such as a mobile phone or tablet.

CROSS REFERENCE TO RELATED APPLICATIONS (Not applicable) This application claims the benefit of Provisional Patent Application No. 62/846,449, fed May 10, 2019, and entitled A System of Using Optical Tags to Conduct Secure Transactions and Authentications, the disclosure of which is hereby incorporated herein by reference.

STATEMENT REGARDING FEDERALLY SPONSORED RESEARCH OR DEVELOPMENT (Not applicable)

BACKGROUND OF THE INVENTION

Today, the manner in which a bricks and mortar transaction is conducted is via cash, credit/debit/gift/store cards, and, if a merchant accepts the same, PayPal from a Point of Sale (POS) device. New technology such as that offered by Apple called ApplePay includes a wireless method of conducting a transaction using NFC (Near Field Communication) chips, POS and wireless protocol. This requires the vendor to use a POS that is equipped with NFC technology. Finally, there are new cloud-based payment schemes such as Venmo, which work by supplying credit/debit card or bank account information, and can facilitate transfer of money without the need to make a physical transaction at a POS device. This technology can facilitate person-to-person transactions, as well as e-commerce transactions.

Online transactions require input of credit/bank/gift/store card information at the point of sale on the website. Certain websites allow the use of Paypal and Amazon services. These services keep all of the credit card information internally for easy use, for example in the case of subsequent purchases.

However, with some of these methods, the use of cards can be a security concern. With methods like Paypal, the need to enter a password is a security concern. With other methods, such as with Venmo, there is no way to locally authenticate the buying and selling parties, which makes POS use, both for e-commerce and brick and mortar difficult and insecure.

In China, almost all consumer transactions use a QR code offered by Alibaba using their service called AliPay. QR codes are insecure but because they are ubiquitous, they have become the de facto standard throughout China. Applications include such a wide diversity of things as admission to a tourist attraction and buying fruit from a local street merchant. Accordingly, QR codes are ubiquitous throughout China. While it has not yet become a serious issue, there are many payment scenarios where it is vital to authenticate the buyer and the seller, and security issues are a potential serious concern in the future.

Given that our world is moving in the direction of ever increasing online activity, identity theft, already very prevalent and causing billions of dollars in damage, aggravation and time spent in undoing the damage, is an increasingly serious concern. A system to by-pass transmitting personal information yet offer the flexibility of conducting important and needed transactions such as self-authentication and purchasing is thus needed to match the increasingly important online paradigm.

At the same time, other threats make the implementation of secure and reliable identification of parties and their actions increasingly important.

SUMMARY OF THE INVENTION

The invention relates to apparatus and methods for securely authenticating information such as the identity of an individual (for example a consumer-user of the inventive system and apparatus), an attribute of the individual, an attribute of information associated with an individual (such as a bank account balance, a medical condition, vulnerability or advantage or a psychological condition), or other attribute of. Such authentication is implemented in the system which may be used for conducting brick and mortar commerce, e-commerce, maintaining a safe environment or the like.

The same is achieved with reference to a secure record. Such use may be in the context of authentications using a mobile device such as a mobile phone or tablet. In addition, the authentication procedure may be used to augment information or change information on a record associated with the individual. The same is facilitated by a multiplex code, which is similar to a barcode a QR code but includes higher density capabilities optionally enabled by nonlinear sub element layouts, multiple colors and multi-shaped multielement sub element components as more fully appears herein.

More specifically, in accordance with the invention, the inventive apparatus may use the camera feature of a consumer user's mobile device or optionally RFID tag recognition device capabilities to securely initiate a transaction with a thereafter authenticated business entity, for example a commercial establishment displaying the inventive multiplex code at the entrance to that commercial establishment. Similarly, the commercial establishment may authenticate the consumer user by reading a multiplex code or other code displayed on the, for example, smart device of the consumer user.

More particularly, it is contemplated that, for example, the consumer user may use a smart device, such as a smart phone, to scan a sticker with a multiplex code adhered to the door of a commercial establishment, causing the smart phone to read commercial establishment identification information and transmit the same to the server of the operator of the inventive system, for example, one accessible as an operator's website over the Internet. The server then transmits an authentication code to the smart device of the consumer user, and that authentication code is displayed by the smart device as a confirmation of the authentication sought. An automatic device or an individual with another smart phone, for example, or other device may then scan the authentication code on the smart phone of the consumer user, to complete the authentication procedure, and thus allow the object of the authentication, such as the charging of an account, admission to a facility, and so forth.

A particular application involves the certification of an individual as having antibodies for an infectious condition, and thus perceived as a low risk for transmission of that infectious condition. More particularly, the object of this particular application is the creation of a safe space where cleared individuals may congregate substantially without a risk of infection or infecting others. Such application is of particular use to, for example, restaurant operators whose employees would wish to avoid exposure to large numbers of individuals potentially spreading an infectious pathogen, such as SARS-CoV-2, responsible for the coronavirus pandemic of 2020. First, in this application, an authentication procedure begins with the individual accessing, for example, the website of the operator of the inventive system and inputting alphanumeric identification information as well as a biometric input, such as a face, fingerprint or other authenticating input. That information is then, together with the alphanumeric information, sent to the operator of the inventive system completing an enrollment process for the consumer user, and resulting in populating the system database with identification information including the biometric input and the alphanumeric information input by the consumer user.

Next, the enrolled consumer user then goes to a medical professional who performs a medical test for the existence of the protective antibodies and the same information is securely certified to and authenticated in the system database. In this particular example, the population of the system database with such medical information completes the medical condition certification process.

Thirdly, once the consumer user is enrolled in the first step of the process and authenticated with the particular, for example, medical attribute, the system uses an authentication process using the multiplex code to allow the consumer user access to the safe space.

In accordance with another embodiment of the invention, a method and system is disclosed which relates to online information transfer via interface surfaces printed or displayed with information and coded data. The coded data may be scanned with an appropriate scanning device. The scanning device communicates with a computer system to authorize the release of information. Together, the interface surfaces, sensing device and computer system are capable of effecting transactions over a network.

The inventive system for the secure transfer of information, enables a user to use a mobile device to securely transfer information using a generated optical machine readable image. In an embodiment, the user scans the encoded, scannable mobile device image that is displayed by the party requesting information (merchant, doctor, other entity) to initiate a transaction. The system completes the transaction by processing information between decryption software residing on either the user's mobile device and/or the computer system, which will authorize release of information through a transaction server or on an application residing on a requestor's device.

The method using a computer-generated code design, referred to herein as a multiplex code, that comprises a plurality of digital tiles or images to authorize payment. A plurality of digital tiles are arranged in a pattern to form a multiplex code-like design, formed as a plurality of "tiles" and functioning as an optically scannable tag. The specific contents of the digital tiles can be decoded using known methods (e.g. static or dynamic codebooks).

The present invention uses a novel identifier called an optically scannable tag that stores an encrypted/hashed message within the optically scannable tag image which is comprised of a unique pattern of digital tiles (formed by elements consisting of one or more pixels), and laid out in a tilework-like pattern. Because it is encrypted/hashed, the message can be considered secure and used to uniquely identify the transaction between parties within an authentication scheme.

The optically scannable tag methodology is also a uniquely secure way of authenticating the optically scannable tag holder and the optically scannable tag scanner. Each party generates a unique and secure time sensitive encrypted/hashed token that is used to authenticate each party. If the tag is dynamically generated, it is, once validated, an authentication of the owner of the tag. The transaction is also authenticated using the optical tag. A camera (e.g. mobile phone camera) scans the tag image and translates it and decrypts it either on the device or on the cloud. This information identifies the transaction (e.g. purchase, validation of users) and is used for further security action in the cloud. The scanning action initiates the transaction.

In principle, the inventive system may utilize a dynamic book. More particularly, an optically scannable tag is requested by one party, for example, the seller. The optically scannable tag is generated (typically in the cloud) and sent to the seller and displayed. The purchaser scans the optically scannable tag using a downloaded application which is associated with the operator of the inventive system. This scan first reads the multiplex code and produces a rasterized image of the same. Using a specified methodology, the rasterized image is translated into a series of digital tiles (e.g., squares)—this may be combined with the next step. Using another specified methodology, the digital tiles are thereafter decoded from their optical view (the colored digital tiles) and stitched into an encrypted/hashed message that can be decrypted and used for the pending transaction or pending authorization.

Alternatively, a static book approach maybe used. For example, a tag may be created in advance and used by the tag owning party to direct a transaction with partial authentication of the tag owning party. The scanning party scans the tag and is given information about the owner, which the scanning party then, optionally, validates in real time outside of the scope of the program (e.g. validate name and address of owner visually).

The dynamic scanning process is novel because it validates each party with their own unique digital mark (e.g. biometric such as a thumb print, face or other personal marker). It is also novel because the transaction itself is authenticated. It is also novel because it is streamlined and does not involve the unnecessary participation of the user. This means that no unnecessary button pressing or the like is needed, beyond pointing to the optically scannable tag and confirming/inputting the transaction. Thus, a purchasing transaction essentially only needs to actions.

Because the user does not enter a password on the electronic device (e.g. laptop) or provide any credit card information to the merchant at the time of purchase, the frailties of security loopholes, present in systems which use such information, are closed to anyone sniffing keystrokes or monitoring transactions on the network.

The scanning process is also novel because it uses optical scanning, optical decoding, message stitching and message decrypting as a means to create ease of use, flexibility of use and security in use.

The optically scannable tag is, compared with conventional QR code, more sophisticated and secure by virtue of its higher information density, as well as its nonlinear pattern and multicolor format. It is noted that security may be enhanced by varying the nonlinear pattern with each transaction, as well as varying the color palette of colors used, thus complicating the task of would be hackers. In preferred embodiments, a multi-colored tag is generated for each transaction where each tag comprises a unique pattern of digital tiles that can be securely sent over networks with decryption only happening on the local device.

Though very useful in financial transactions, this system may also be used as a conduit to transmit other critical data dynamically (e.g. medical data), particularly in the context of creating safe environments as detailed above.

Thus the inventive system is capable of application in the most challenging of environments where security is of paramount important for a transaction, or for other aspects of human interaction.

In accordance with the invention, a method is provided for authentication applicable, for example, to controlling access to a space. A plurality of sets of consumer user identification information associated with a plurality of consumer users are received and stored in a consumer user database. A plurality of biometric identifiers, each of the biometric identifiers being associated with an associated one of the plurality of consumer users are received and stored in the consumer user database with associative information associating each biometric identifier with its associated consumer user to form an enrollment record. Verification is made of the identity of a presented individual by receiving a presented set of consumer user identification information from the individual whose identity is to be verified, acquiring a locally generated biometric identifier of the type stored in the consumer user database directly from the individual whose identity is to be verified, comparing the presented set of consumer user identification information to the sets of consumer user identification information stored in the consumer user database to determine whether there is a match between consumer user identification information stored in the database and the presented set of consumer user identification information, and comparing the locally generated biometric identifier to biometric identifiers stored in the consumer user database to determine whether there is a match between biometric identifiers stored in the consumer user database and the locally generated biometric identifier.

A comparison verification signal is generated in response to the determination that the presented set of consumer user identification information and the locally generated biometric identifier match a set of consumer user identification information and its associated biometric identifier. A certification procedure is performed with respect to the presented individual to generate a certification result. The certification result is stored in the consumer user database. A particular communications device associated with a particular consumer user is provided, in response to a request originated from the particular portable communications device with an identification signal in a format which may be read by a device at a commercial or social establishment is a verification that the consumer user has been verified. The particular consumer user is then provided with access to the establishment.

The plurality of sets of consumer user identification information associated with a plurality of consumer users may be stored in memory associated with a server operated by a website operator, and wherein the storing is implemented by transmission to the server over the Internet.

The biometric identifiers are stored in memory associated with the server and the communications device of the user consumer may be a portable communications device.

The above verification steps may be performed by a certified service provider's accessing the server of the website operator over the Internet.

A certification procedure may be performed with respect to the presented individual to generate a certification result by performing a psychological interview.

The certification procedure may be performed by verifying a balance in a monetary account maintained by the consumer user, and such action may be followed by the charging of a monetary amount to the monetary account maintained by the consumer user.

The establishment may use a publicly displayed and publically accessible coded information device, and the request may be generated in response to reading of the coded information device by the particular portable communications device associated with the particular consumer user.

The coded information device may be a coded graphic which identifies the establishment, and wherein the particular portable communications device associated with the particular consumer user transmits identification information to the server of the website operator. The server operated by the website operator, in response to the reception of the transmitted identification information associated with the establishment and identification information associated with the particular consumer user, may transmit an admission signal to the establishment.

Optionally, the coded graphic may have a nonlinear layout and multiple colors. The layout may be varied from transaction to transaction. Likewise the pallet of available colors for the coded graphic may vary from transaction to transaction with the object of complicating any attempted breach of the security of the system.

The admission signal may operate a lock at the door of the establishment to allow entry to the establishment by the particular consumer user.

Optionally, the establishment may be an automobile for hire and the lock may be an automotive door lock.

The identification information may be transmitted to the server over the Internet, causing the server to transmit a code which is optically displayed on the particular communications device, and the code on the phone maybe scanned at the establishment and in order to unlock the door to the establishment.

BRIEF DESCRIPTION OF THE DRAWINGS

The operation of the inventive system and its methodology will become apparent from the following description taken in conjunction with the drawings, in which:

FIG. 1 illustrates a multiplex code in accordance with the present invention;

FIG. 2 illustrates an alternative multiplex code;

FIG. 3 illustrates shapes which may be employed in the tiles of the inventive multiplex code;

FIG. 7 illustrates yet another pattern for a multiplex code in accordance with the invention;

FIG. 8 illustrates other types according to the present;

FIGS. 9 and 10 illustrate optical bit encoding in accordance with the invention;

FIG. 12 illustrates examples of usage of the inventive method;

DETAILED DESCRIPTION OF THE PREFERRED EMBODIMENTS

The present invention is based around optically or wirelessly scannable multiplex codes composed of an enclosed shape defined by a frame which guides the software to the relevant scanning area, as shown in FIGS. 1 and 2. The border is the outermost solid rim of the tag.

As shown in FIG. 3, it is understood that the design can be various shapes hexagonal, square, triangle, pentagonal, septagonal, octagonal and onwards to an increasing in number of sides infinitely and also not limited to polygons (e.g. semicircles, as shown in FIG. 3).

The multiplex code is comprised of a unique pattern of digital tiles (similar to a multiplex code using real tiles) to form a pattern or picture. FIG. 2a demonstrates an example of a digital tile.

Figure 4:
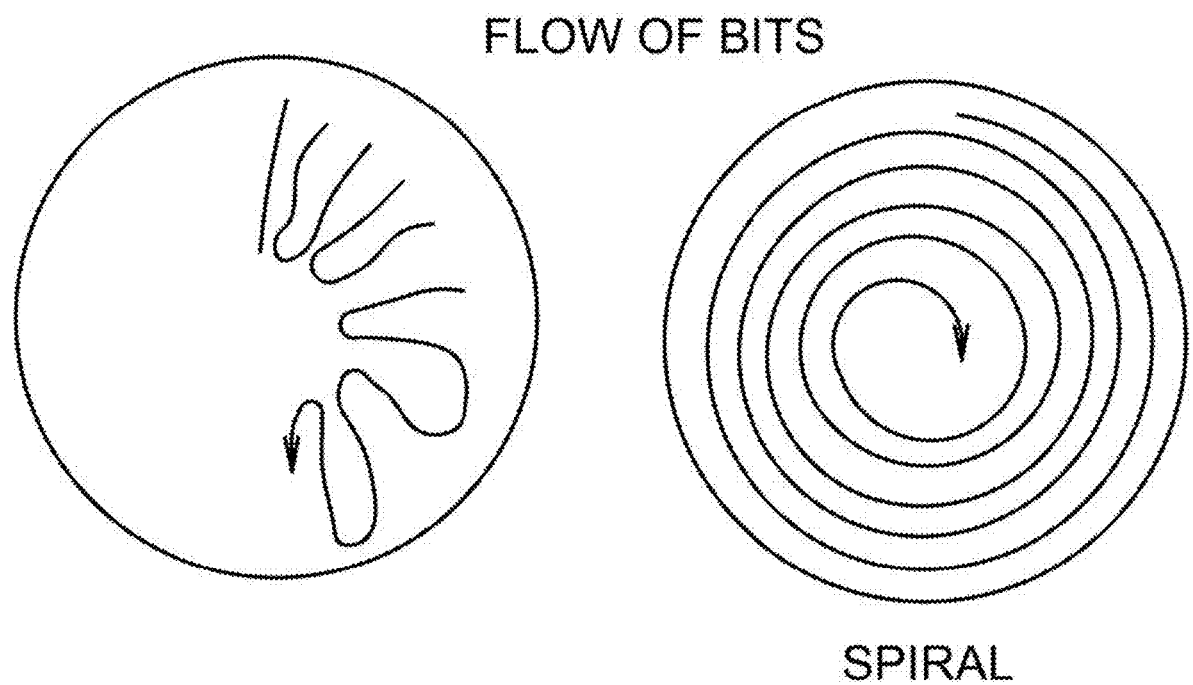
FIG. 4 illustrates in and out and spiral patterns of tiles according to the present invention.
Figure 5:
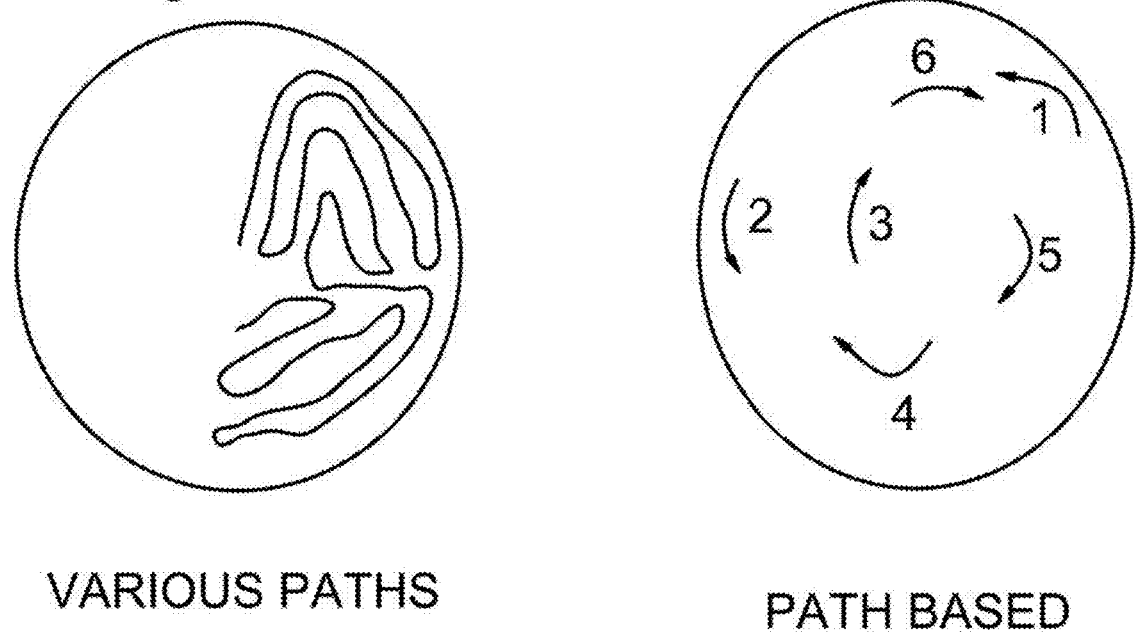
FIG. 5 illustrates various path and path based patterns of tiles according to the present invention.

The possible composition, arrangement and number of the tiles are infinite. For example in FIG. 2c, the tiles are squares in an outward-winding circular pattern. Alternatively, the tiles may flow outward to the outer rim and turn around to come back in to the center, then return out again till the pattern is complete (see FIG. 4). The tile pattern may include, but is not limited to, the form of shapes such as triangles, circles or squares, stars or hearts.

Figure 6:
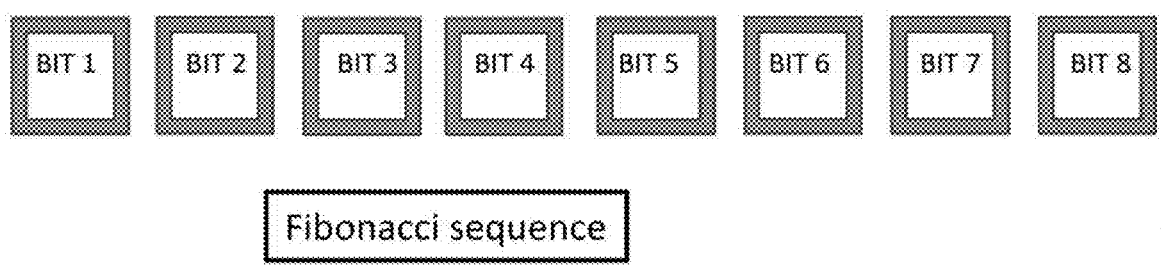
FIG. 6 illustrates the extraction of bits.

The tiles in the scanned tag are uniquely arranged by the mobile device or within the server into a hashed/encrypted message. The methodology used for stitching these frames can vary and includes but is not limited to sequential, pattern-based, algorithm-based (example given in FIG. 6). The optical winding of the frames and the stitching together of these frames are two separate decoding steps. Both use similar encoding means shown in FIG. 4.

The extracted message size can be variable—based on encoding parameters. This variable message size may vary the number of tiles. A smaller message is shown in FIG. 1 and a larger message is shown in FIG. 2.

The tiles are shown as squares but they may take the form of any geometry (see FIGS. 3 and 8). The tiles may also be in the form of alpha numerics and symbols such as an exclamation point, heart sign or a smiley face, as shown in FIG. 9. These tiles may also be in the form of a picture or animation. As shown are square frame that are encoded with colored triangles. Any color may be used and instead of triangles, other shapes may be used to generate a frame. A uni-color outline of a frame and the geometry that forms the frame may be used as well.

A color pallet is included in the center of the multiplex code and a series of color pallets are included at the edge of the tag, as shown in FIG. 7. This feature is meant to correct for changes in the environmental color, lighting and shading due to shadows, which may cause a localized discoloration of the multiplex code. The color palettes around the multiplex code and in the center of the multiplex code prevent color variance, shade and glare problems. Each palette of color anchors the colors of the local blocks near it.

Figure 11:
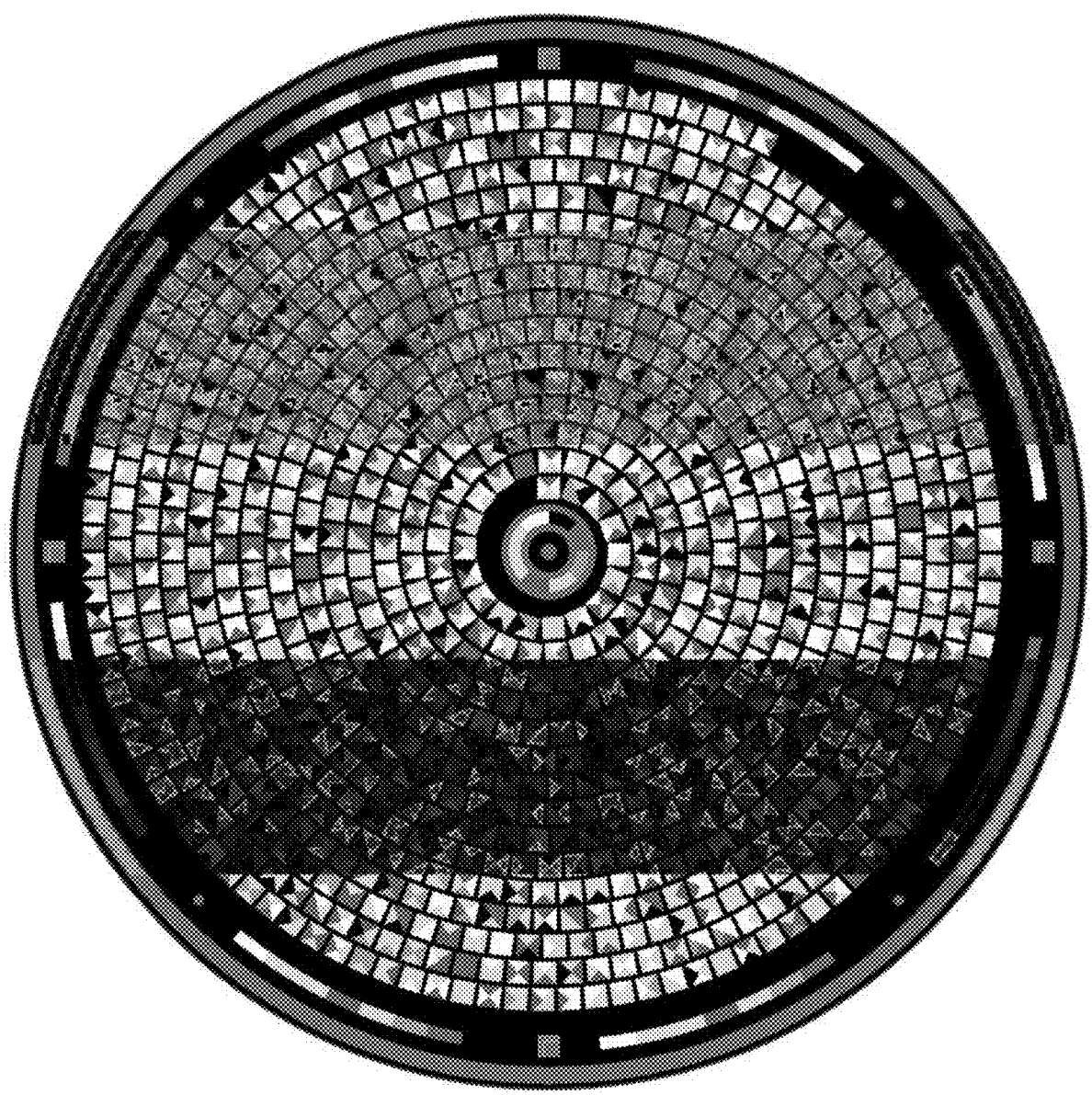
FIG. 11 illustrates an alternative embodiment of multiplex code of the present invention.
Figure 13:
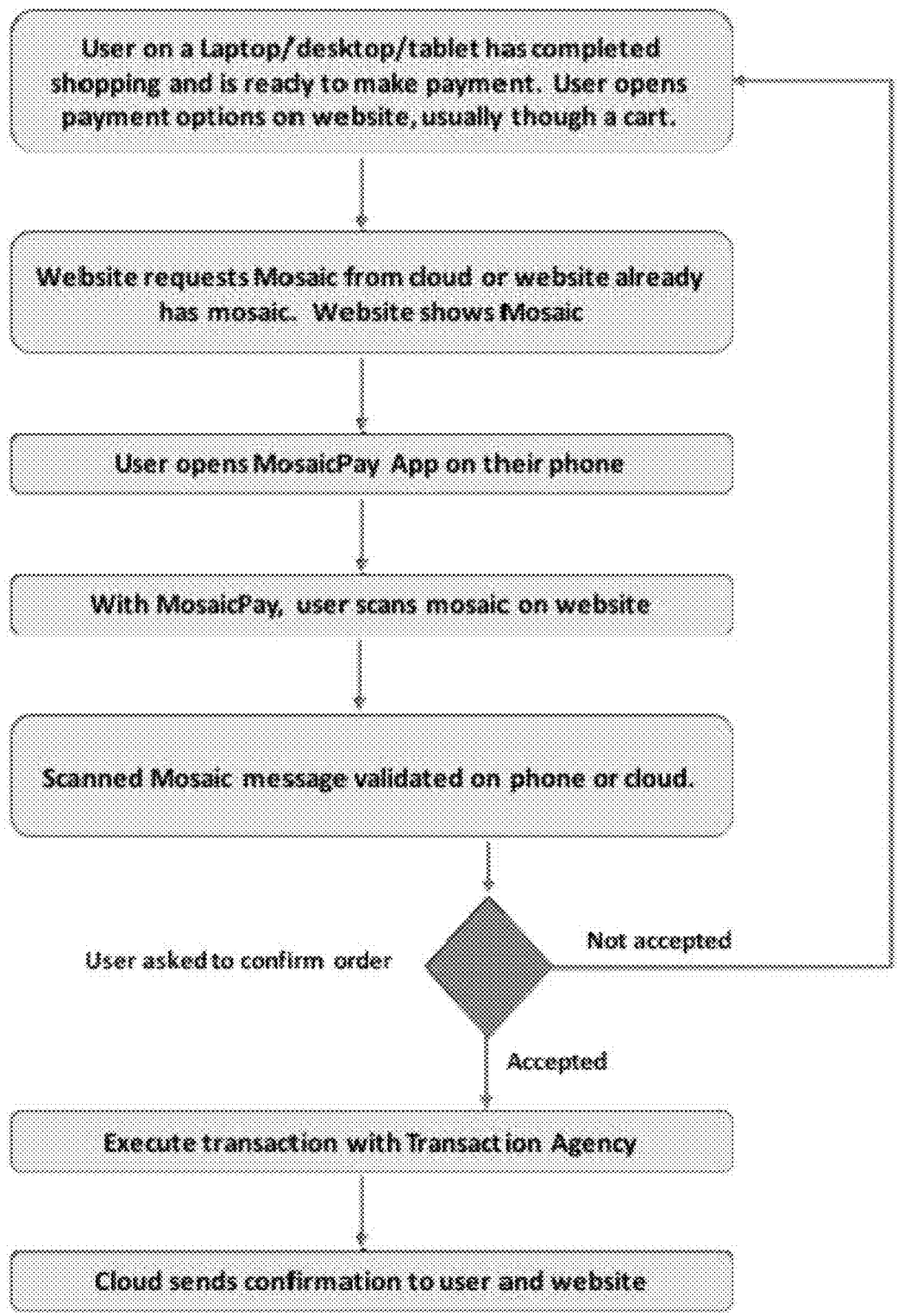
FIGS. 13-20 is a flow chart generally illustrating a general implementation of the present invention.
Figure 14:
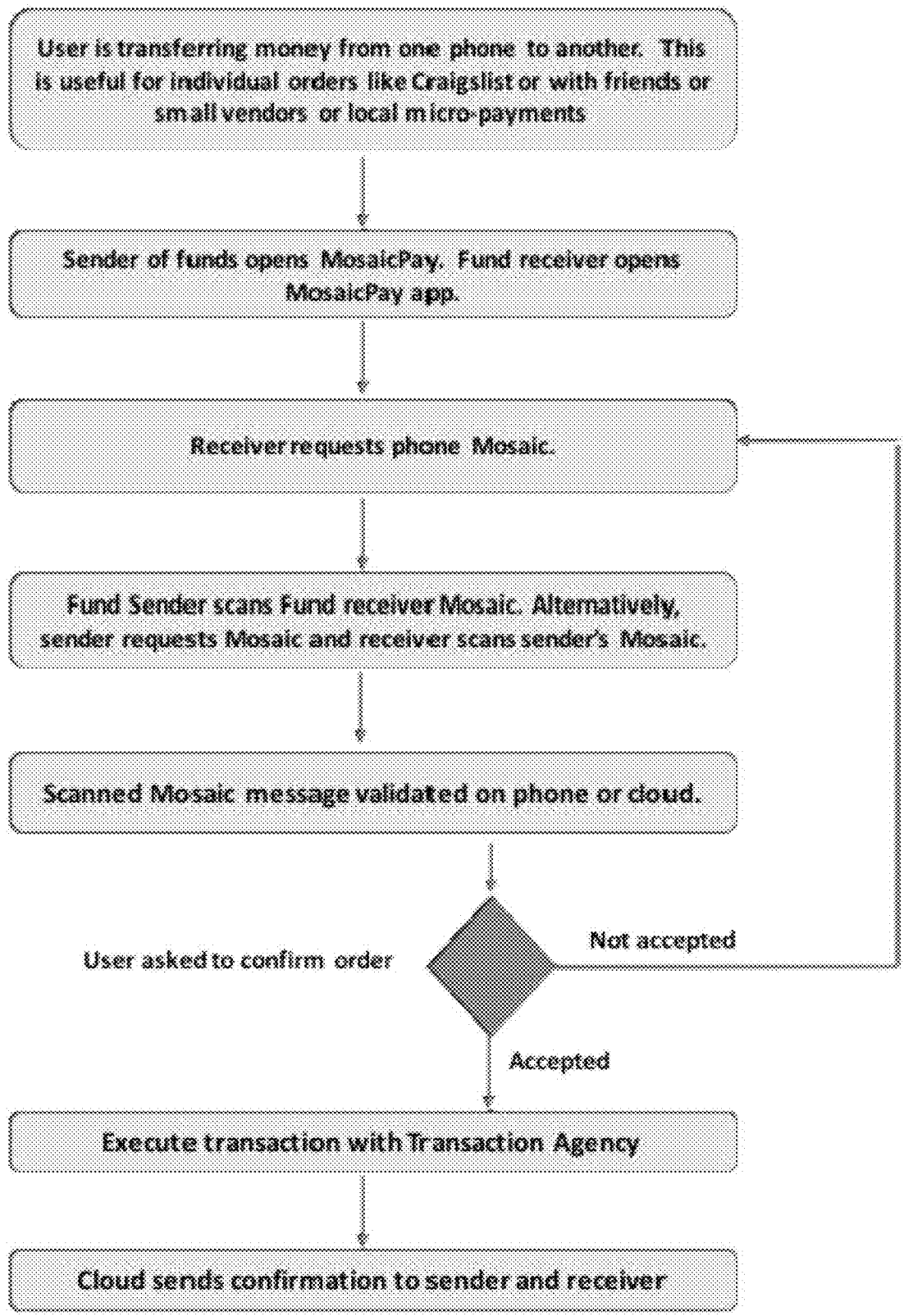
Figure 15:
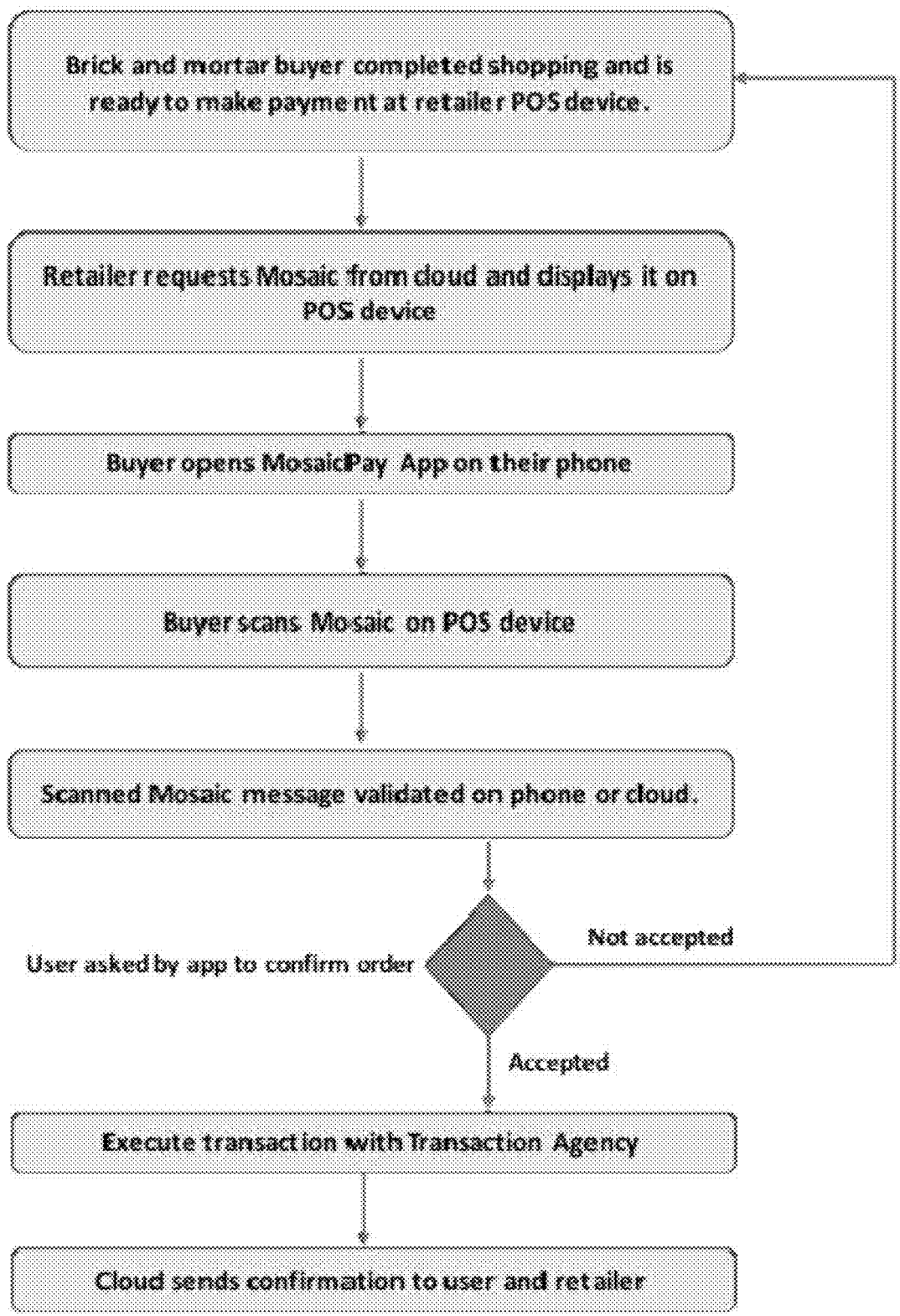
Figure 16:
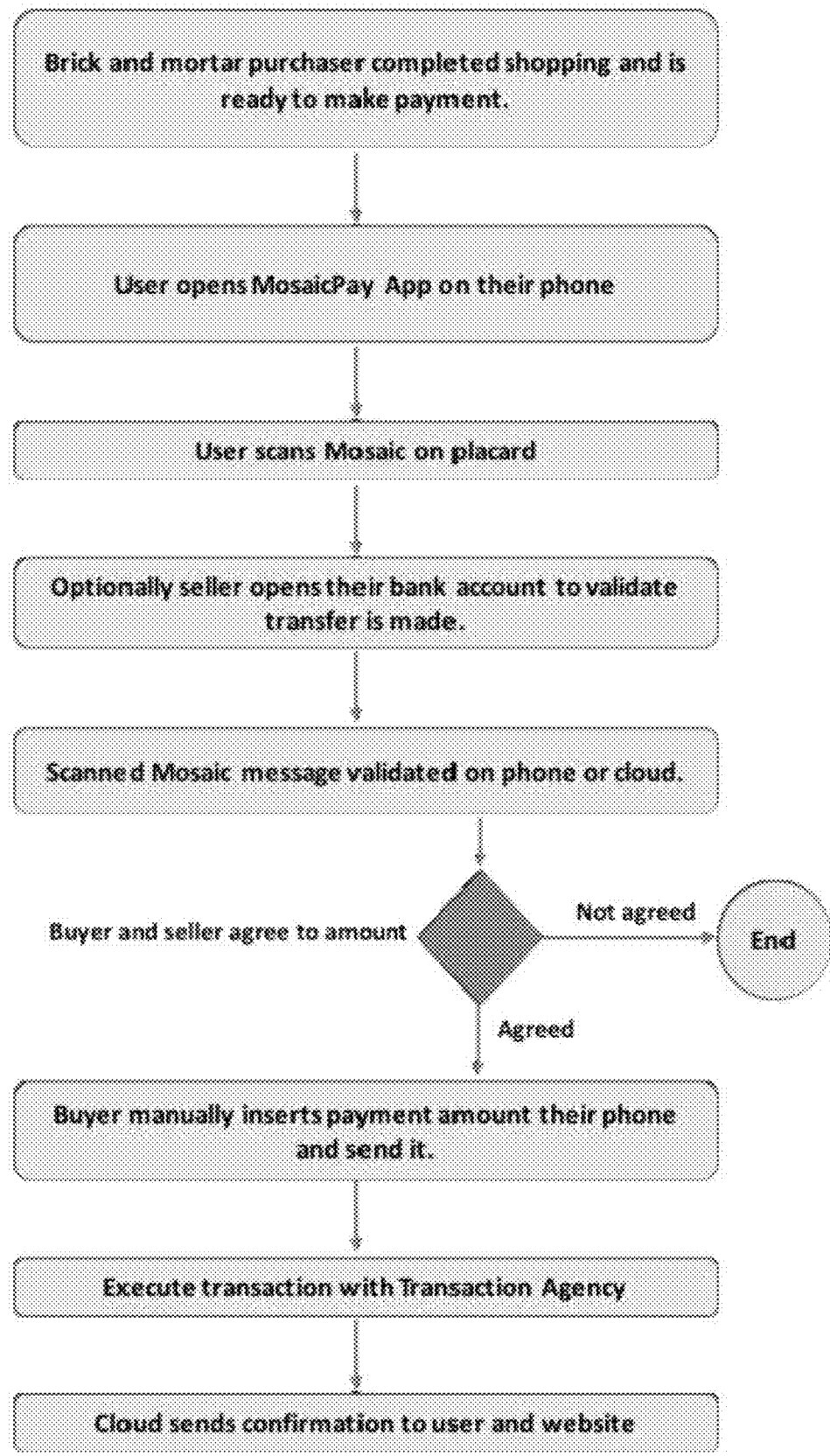
Figure 17:
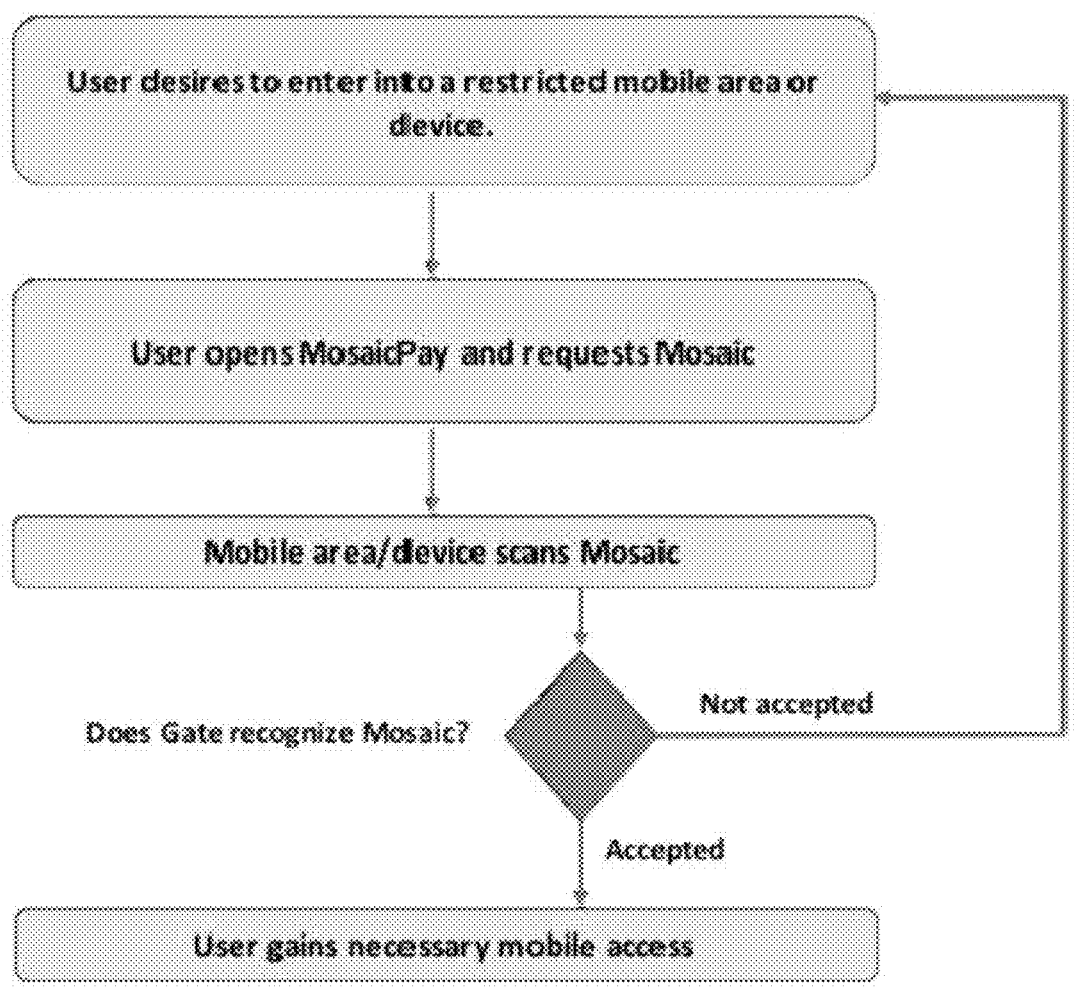
Figure 18:
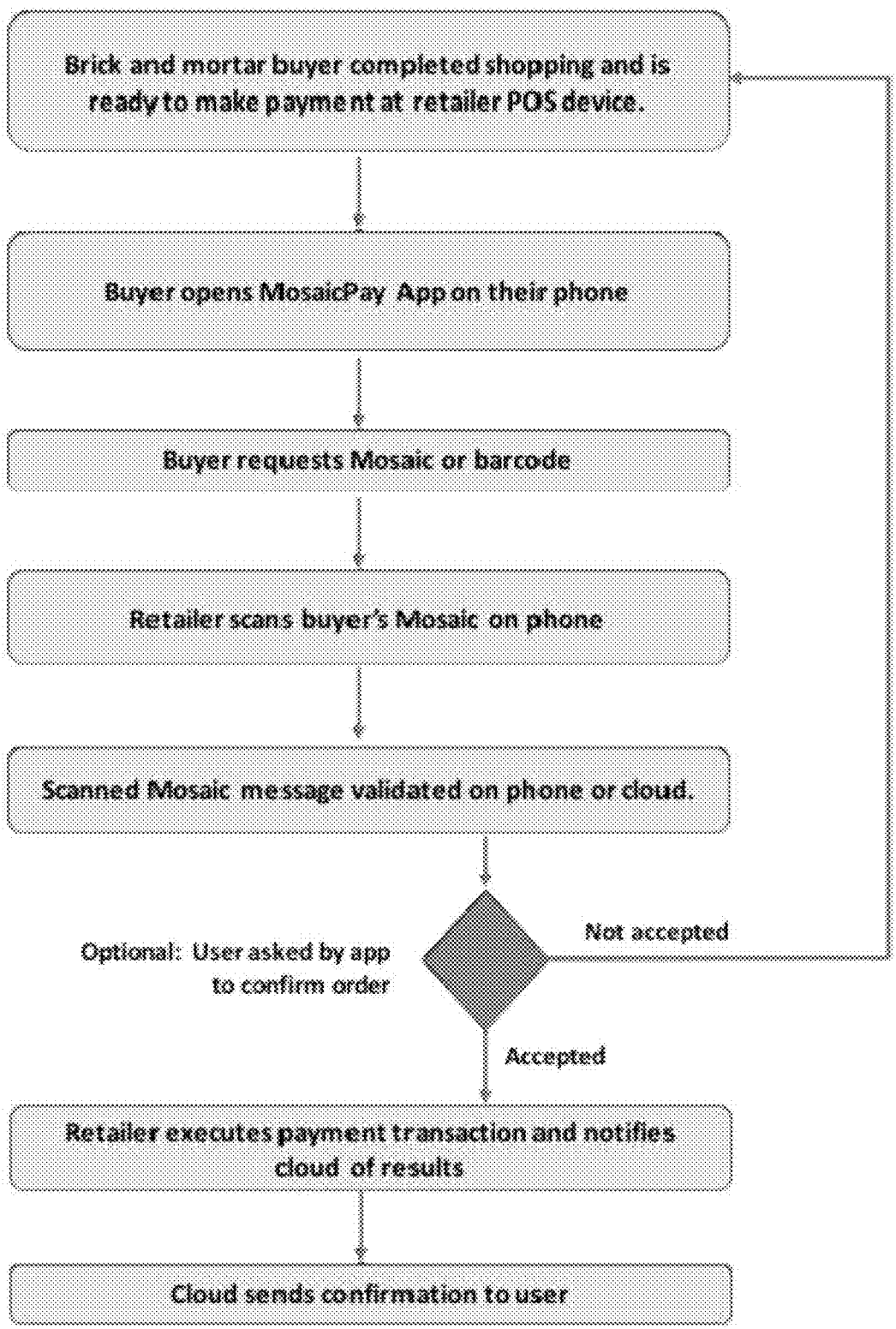
Figure 19:
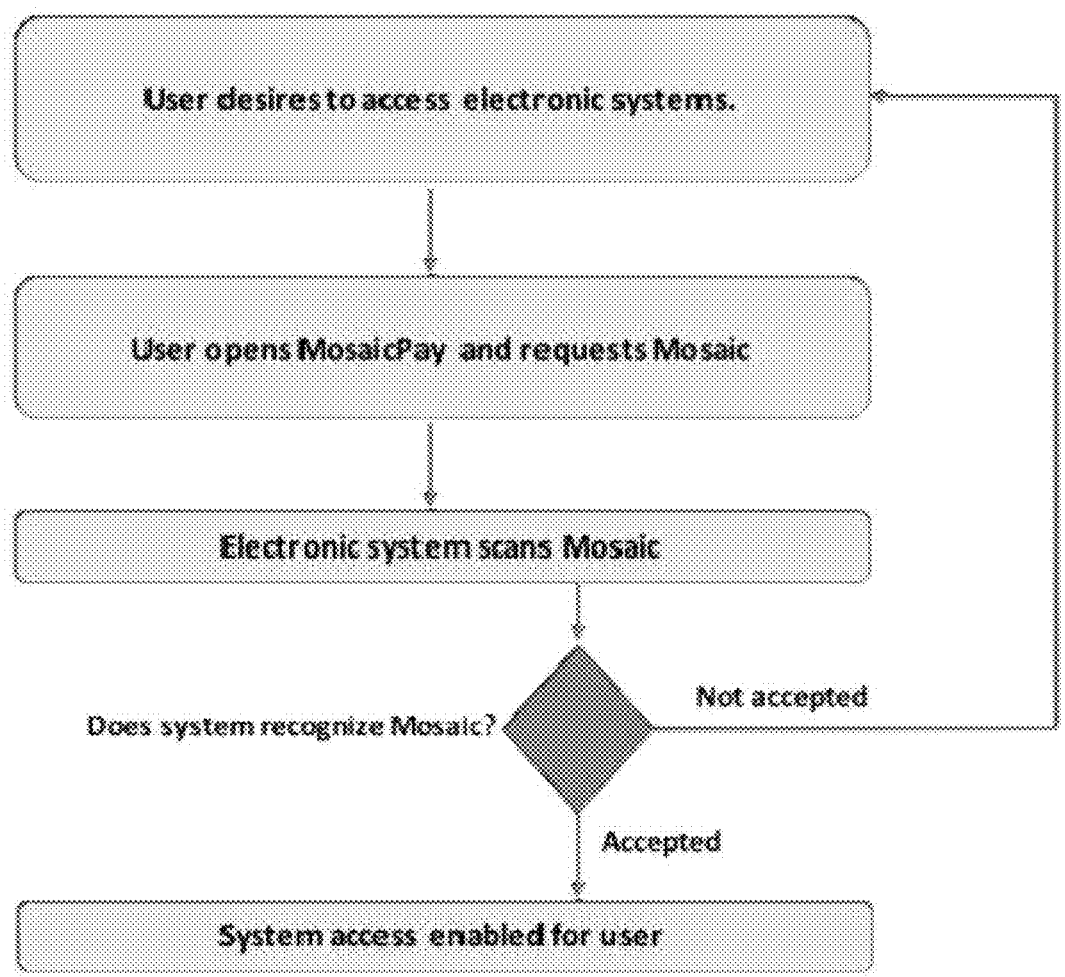
Figure 20:
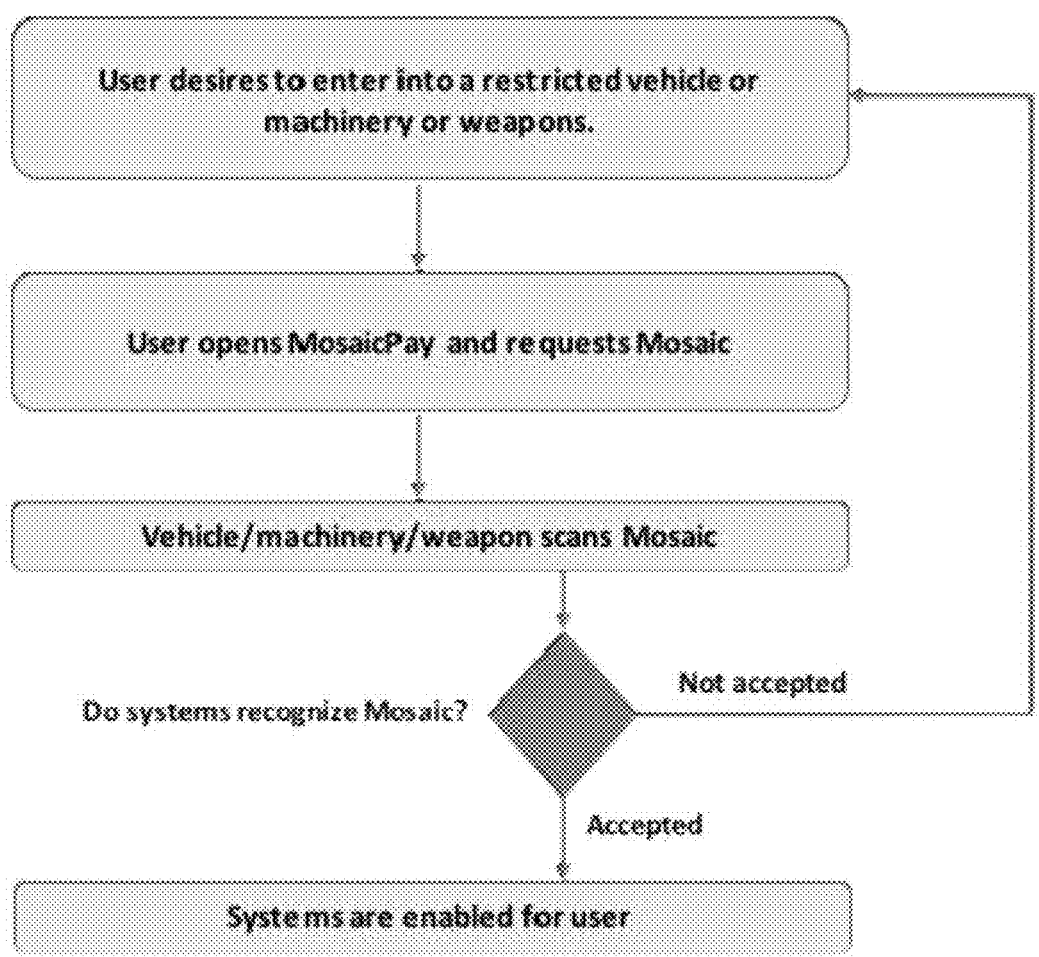
Figure 21:
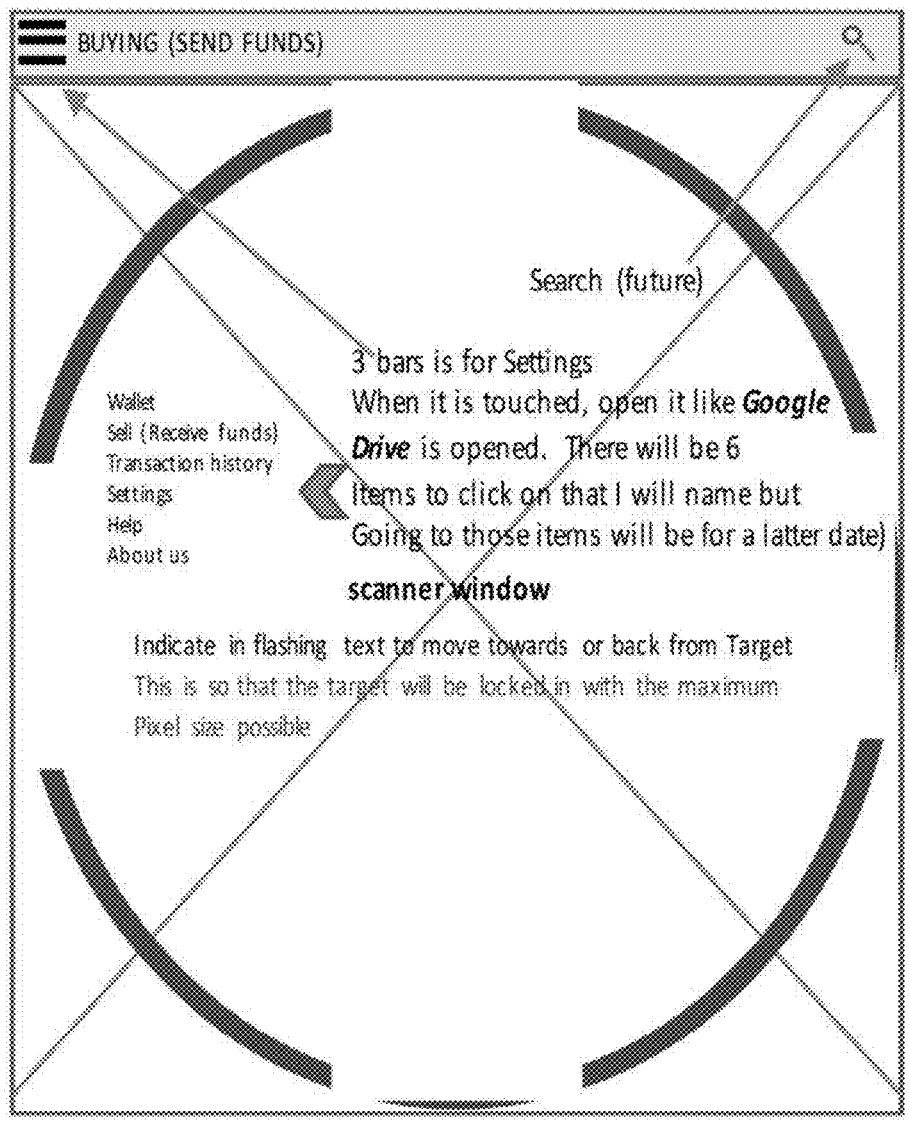
FIG. 21 illustrates an app screen according to the present invention.
Figure 22:
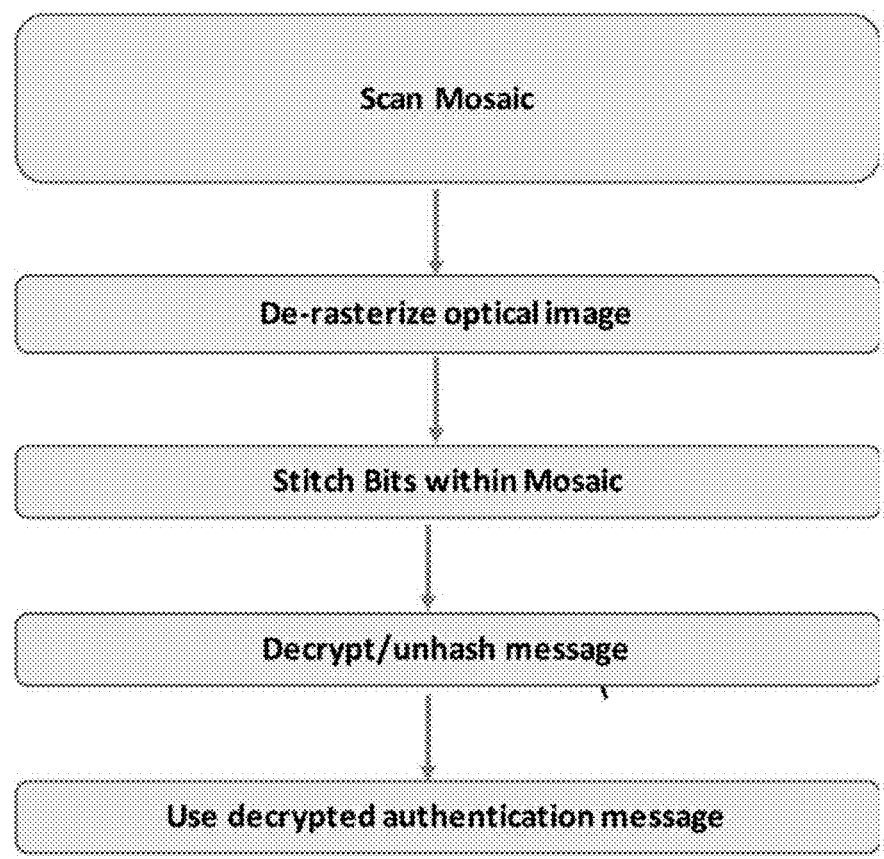
FIGS. 22 and 23 illustrate a multi-party methodology for the present invention.

This multiplex code may also be without any color, as shown in FIG. 11. This would make it black, white and grey as needed.

Associated software generates unique multiplex codes on a secure server on demand, based on specific requests of authorizer receivers of multiplex codes. Depending on which type of user is requesting the multiplex code, a different type will be made for the specific request. For example, if a 500 pixel width multiplex code is requested by a point of service device to be valid for only 30 seconds, a small multiplex code with the appropriate security messaging will be made to enable that specific multiplex code request. That multiplex code will be invalid after 30 seconds, or some other period of time, of generation and/or receipt.

The multiplex code may be dynamic and rotate and switch frames with a variable time frame. For certain high security applications, new multiplex codes may be requested at specified intervals of time. A new multiplex code will be transmitted by the generator at each interval. The changing nature of rapidly generated multiplex codes means that any hacker would have to start from scratch hacking into each new multiplex code, hence mitigating any chance at hacking to the tag.

The tag can hold forms of identification including a unique ID for the requestor or ID for the request (not only the requestor). The message contained in the tag may hold the time/date it was generated and the interval for which it is valid. The message contained in the tag may hold location information of where the multiplex code is being used in the transaction. The message contained in the multiplex code may hold financial information including but not limited to amount of payment requested by seller. The message contained in the multiplex code may hold seller information including but not limited to name. ID and table location, seating location.

The message contained in the multiplex code may hold part or all of an encryption or hash key. This key may be used in the transaction process to provide further security. The multiplex code may be scanned in part or whole as a rasterized image.

In some embodiments, the multiplex code may be scanned frame by frame instead of a frame map. In other words, the scan recognizes the frame within the multiplex code being scanned and scans it as a character rather than an optical frame map.

In other embodiments, the multiplex code may be scanned in pre-defined component parts, such as some of the frames but not all of them.

For some applications, data on the multiplex code may be replicated in the multiplex code multiple times for reliable usage. Replication of data ensures that challenging lighting and angles of the scan will not corrupt the multiplex code information being scanned. The multiplex code borders and specific orientation points in the multiplex code may be used to recognize and orient the tag by the scanner.

In preferred embodiments, access to the application is only through a secure authentication method such as biometric identification including but not limited to thumbprint, retinal scanner or facial recognition.

In other embodiments, the tag may be an animated projection of a 3D model. Data can be stored more efficiently, more densely and more security as a 3D model. Once the software is activated, it opens straight to either the send fund screen or receive screen. The send fund screen automatically is set to scan for multiplex code—no button is needed to accept a multiplex code. The simplicity of scanning and executing the transaction is novel.

Figure 23:
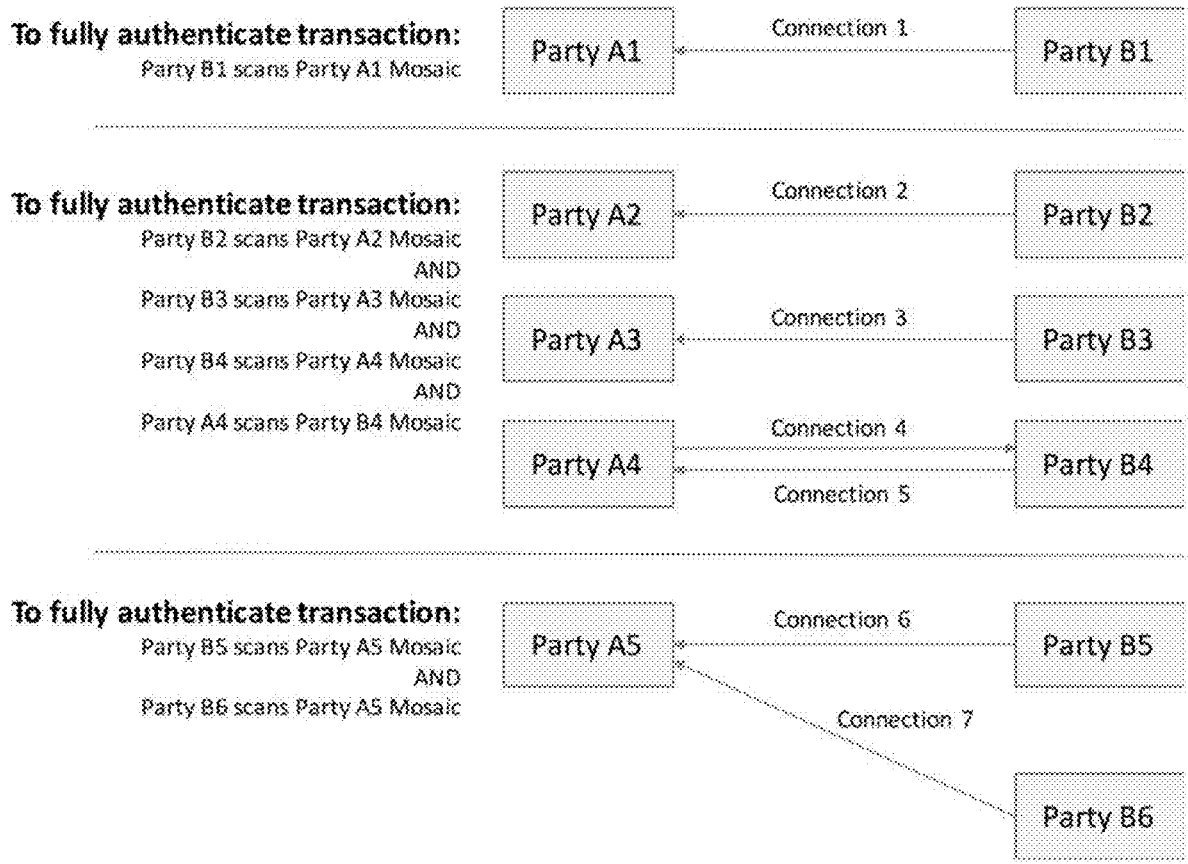

The multiplex code system can be used to authenticate 2 or more parties by scanning one parties multiplex code with another's multiplex scanner. There are two types of scanning for authentication, static and dynamic. Dynamic scan is a real-time multiplex code being scanned (scanning device scans a screen which contains a recently requested multiplex code). Dynamic scan is a real-time multiplex code being scanned (scanning device scans a screen which contains a recently requested multiplex code). Party A requests a multiplex code from a cloud based generator and displays it on their screen. Party B scans the multiplex code in real time. Party B decodes the optical image and optionally decrypts image. This information is transmitted securely to the server, where, if it has not been decrypted on the scanning device, it is decrypted. Party A is validated hereafter or when Party A requests a tag. Party B is validated here. Party C may optionally have scanned party A or another party (D), as shown in FIG. 23. The unencrypted/unhashed multiplex code along with the parties' authentication is used to validate the transaction.

For static scanning, the scanning device scans a pre-printed multiplex code (on a physical object) or permanent/long-term active tag (onscreen). Party B is authenticated in the same manner as dynamic scanning. Transaction is validated in the same manner as a dynamic scan. Party A is validated by unencrypting the hash/encryption and displaying identity data for user to validate physically. For example, if someone is selling bananas at a particular address location or perhaps a license #, the multiplex code will be used to derive this information. Party B may be given this information to validate and confirm Party A.

The authority and ability to generate a tag may reside with various unrelated groups for their own purposes such as companies, government agencies or military groups. The tag generating database may be used as a value-added cloud function. The API is a novel way to interface with an optical scan authentication clearinghouse. In certain embodiments, the system may have the ability to aggregate the approval of more than one scan with one more party A and one or more party B because a transaction can take place, as shown in FIG. 23.

The tag client scanning and encryption software may be integrated into other apps. This is a novel way to easily and quickly create security for the targeted app and app environment.

Encryption keys can be broken into multiple portions and saved in different locations to prevent usage of the key in case of unauthorized access to the key database. The multiplex code can also be used as a temporary ID, with it having an expiration period that may or may not be embedded in the multiplex code.

The newly generated multiplex code, with their nearly impossible to duplicate composition as well as the associated expiration times, lead to a secure transfer of information that is not currently available without the hassle of elaborate encoding and decoding systems. Any two parties with the associated software or phone application can easily transfer information back and forth. The sending party generates a temporary multiplex code, the receiving party receives it and authorizes the transfer of whatever information is needed.

The scanning of the multiplex code itself can be done in a number of ways including but not limited to a mobile device scanning a multiplex code from a website, a mobile device scanning a multiplex code from another mobile device, a mobile device scanning a multiplex code from a point of sale device, a mobile device scanning a physical tag to identify the location of mobile holder and/or initiate purchase; a stationary entry point scans a multiplex code from a user's phone or physical ID tag, a mobile entry point scans a multiplex code from a user's phone or physical ID tag, at POS, a user scans multiplex code to conduct a transaction, a multiplex code scanner is used to give entry to electronic systems, for security/military use the system statically and/or dynamically acting as a gatekeeper for entry or gatekeeper for operating machinery, weapons, vehicles, instruments, and appliances.

Respecting the information density required to keep the system secure, it is noted that security comes from a hacker not knowing how the optical encoding works (security through super obscurity). This implicates what the characters are to identify and the order the characters. In addition, security may be obtained through. More particularly, the encryption/cash may be achieved through existing encryption technology.

Generally, amount of data that can be stored in the inventive multiplex code is one-third of the theoretical maximum capacity of the multiplex device. This is the case because substantial capacity is devoted to achieving redundancy. In accordance with the invention, the same message in the inventive multiplex code may be subjected to comparison with the taking of the two that are equal. This is because if the multiplex code is damaged or it is not in a good lighting situation, the inventive multiplex code can still be read.

The inventive system can store an unlimited size of data. It depends if the size of screen, thus the width of the multiplex code. A 500 pixel diameter multiplex code will store about 500 bytes of data.

In respect to the amount of information required to keep the system secured, this depends on the encryption used and is generally understood by those of ordinary skill in the art and not a part of the invention.

The independent dynamic multiplex code cannot be easily aliased because the phone sends a token (an encrypted message) to the multiplex code generator which authenticates the user, then sending a multiplex code to the authenticated requesting party to be scanned by the second party. This token can be generated using the biometric data of the requesting user as one of the variables to encrypt the message so it cannot be aliased.

The inventive printed multiplex code cannot authenticate by itself. The system is designed in this manner because a multiplex code device can be copied. More particularly, the system is safeguarded against such misuse because the printed multiplex code has other data (for example where this multiplex code is located). Optionally this data may be displayed to the user. If it does not visually match, the user is advised to walk away.

In accordance with the invention, users generate tokens which gets validated by the server. Both users must log in using a biometric because only a biometric will allow validation of the user.

In accordance with the invention, the image encryption procedure comprises encoding encrypted information into the image. More critically, the information is compressed (e.g. zipped). The information is repeated, for example, three times. Some additional metadata such as the intended length is injected into the encrypted message. The information is encrypted by masking it with a hash-generated string, using the Sovereign algorithm.

The information may then be rendered into an image, for example as above. This may entail, for example by using a violet colored circular outer boundary and center which is drawn to contain the encoding. Color and placement registration marks are added to assist later decryption. The encrypted information is broken up into individual characters. Each character is expressed as a square divided into 4 regions of 8 possible colors each. These squares representing the message data are arranged in a spiral pattern around the center out to the boundary.

In accordance with the image decryption procedure, retrieval of the encrypted information obtaining a photograph of the image. The violet circular boundary, and center are identified within the image. The software determines which way is "up" by utilizing various registration marks. The software assesses the roundness of the image and adjusts for perspective. The software determines the lighting in the image, so that the expected coloring can be anticipated. In accordance with the invention, the software locates and "reads" each of the squares in the spiral around the center.

In accordance with the invention, the message is unencrypted using the Sovereign algorithm in reverse, unmasking the encrypted message with a hash-generated string. The metadata is validated to ensure proper decryption. The message length is derived from the metadata. The three repetitive copies of the message are separated back out of the message. The three message copies are compared against each other and used for noise and error correction. The best corrected message copy is decompressed (unzipped), resulting in the original decrypted information.

In accordance with the preferred embodiment, the hash-generated strings above used for encryption and decryption are identical. It is noted that identical strings can be generated independently in separate locations by using the same password as the "seed" for the hash.

A particularly preferred embodiment of the present invention will now be described with reference to FIGS. 24-28.

As alluded to above, one of the applications of the inventive multiplex code is in the structuring of and access to a controlled space, and, more particularly by way of particular example, a space where consumer users would be protected from individuals at a higher risk of transmitting infectious pathogens. In accordance with the invention access to such a safe space is limited to people who have been certified in accordance with the requirements for that space.

This object may be advanced by, for example, limiting certification to individuals who have tested positive for an antibody and are therefore unlikely to be transmitters of the pathogen which caused the disease which in turn resulted in production of the antibody by the consumer user's immune system.

By way of another example, certification of the administration of a standard or specialized set of vaccinations may be used to limit access to educational institutions or facilities. Most primary, secondary, and post-secondary schools require students to receive certain vaccinations or receive a certified exemption to attend school. The certification provided by the present invention may be used to grant students access and could also easily be used to certify staff or any contractors, providing a convenient method to protect students which is not otherwise currently feasible.

By way of another example, certification of a prescription for a particular drug or other treatment may be used to authorize the dispensing of drugs to a patient at a pharmacy, medicinal cannabis dispensary, or other establishment.

While the above example uses the criteria of, for example, having an antibody or collection of antibodies) indicative of a small probability of transmitting pathogens, for example highly contagious or dangerous pathogens, other criteria may be used, for example social, philosophical or other criteria.

By way of example, certification at a daycare center may be limited to children who have been examined by a psychologist and found to have a predisposition for cooperating and working with peers, nonviolence and inquisitiveness. In this way parents could put their children into an environment where their personal objectives for the development of their children may be met.

By way of another example, certification may be based upon a moral or religious viewpoint, or more generally a philosophical viewpoint whether or not it is associated with an organized religion. In this case, certification would be key to the particular objectives and such certification would be provided by an appropriate professional, for example a clergyman.

Figure 24:
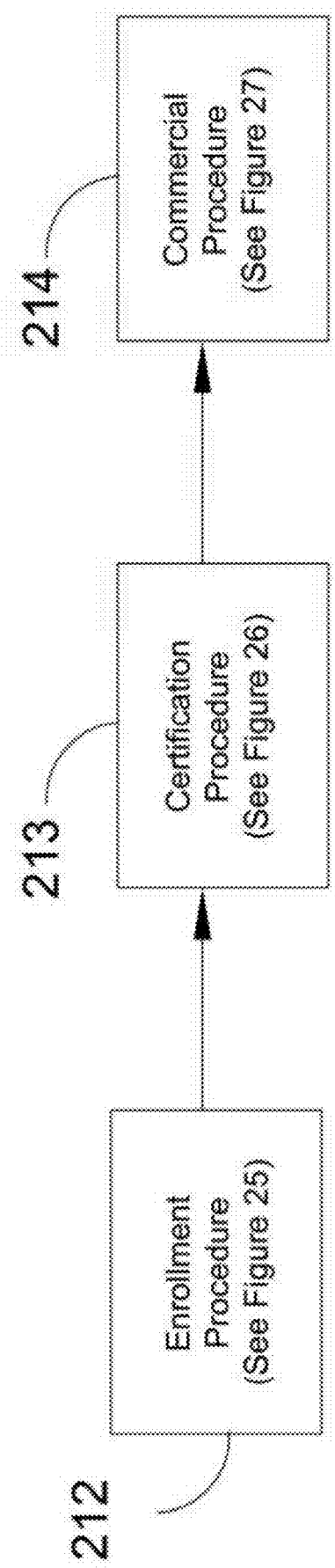
FIG. 24 illustrates the overall inventive method in the context of the creation of safe commercial spaces.

Generally, with reference to FIG. 24, the above objectives are achieved in accordance with inventive method 210. Method 210 comprises three separate portions. More particularly, in accordance with the invention, the inventive method is initiated with an enrollment procedure 310, where consumer users register with the operator of the inventive system. Enrollment procedure 310 is followed by a certification procedure 410. During certification procedure 410, consumer users who have successfully competed enrollment procedure 310 are certified by an appropriate professional, for example, in the case of the promotion of an environment where the transmission of undesired pathogens is low, that professional would be a medical doctor or other health professional trained in the certification procedure, for example, a nurse practitioner.

Following completion of enrollment procedure 310 and certification procedure 410, the inventive system enables an enrolled and certified consumer user to engage in a particular commercial activity by sequencing through the steps in the execution of a commercial procedure 510. This allows the user to gain access to a controlled space, for example a restaurant, a tennis court, a swimming pool, a maker space in a library, a town meeting, an entertainment facility, and so forth.

The invention also contemplates controlling access to mobile venues, for example, a carpooling service or a taxi service such as Uber. It is also noted that, in accordance with the present invention, access to virtual venues may also be controlled.

During enrollment procedure 310 the user registers personal identifying information and biometric data, which is stored in a cloud server for future use. Once enrolled, the user goes through the certification procedure 410, which is executed in conjunction with the entry of certified medical or other information into the user's profile on the cloud server operated by the operator of the inventive process 210.

The next step in the process is the implementation of a particular, for example, commercial transaction or, perhaps more accurately, event or service implemented during the portion of inventive process 210. This portion of the inventive process 210 is designated herein as commercial procedure 510. Completion of commercial procedure 510 results in allowing the user to gain access to, for example, commercial facilities such as restaurants, retail establishments, sporting venues, automobiles, or other physical establishments requiring certification prior to admission, such as medical certification or other certification to gain entry by securely transmitting confirmation of the user's information via the inventive technology.

In accordance with the invention, for example, entry may be physically barred. More particularly, the user may be obligated to present his smart phone to, for example, a person on the other side of the glass door or a car window in order for mechanical lock to allow access.

Figure 25:
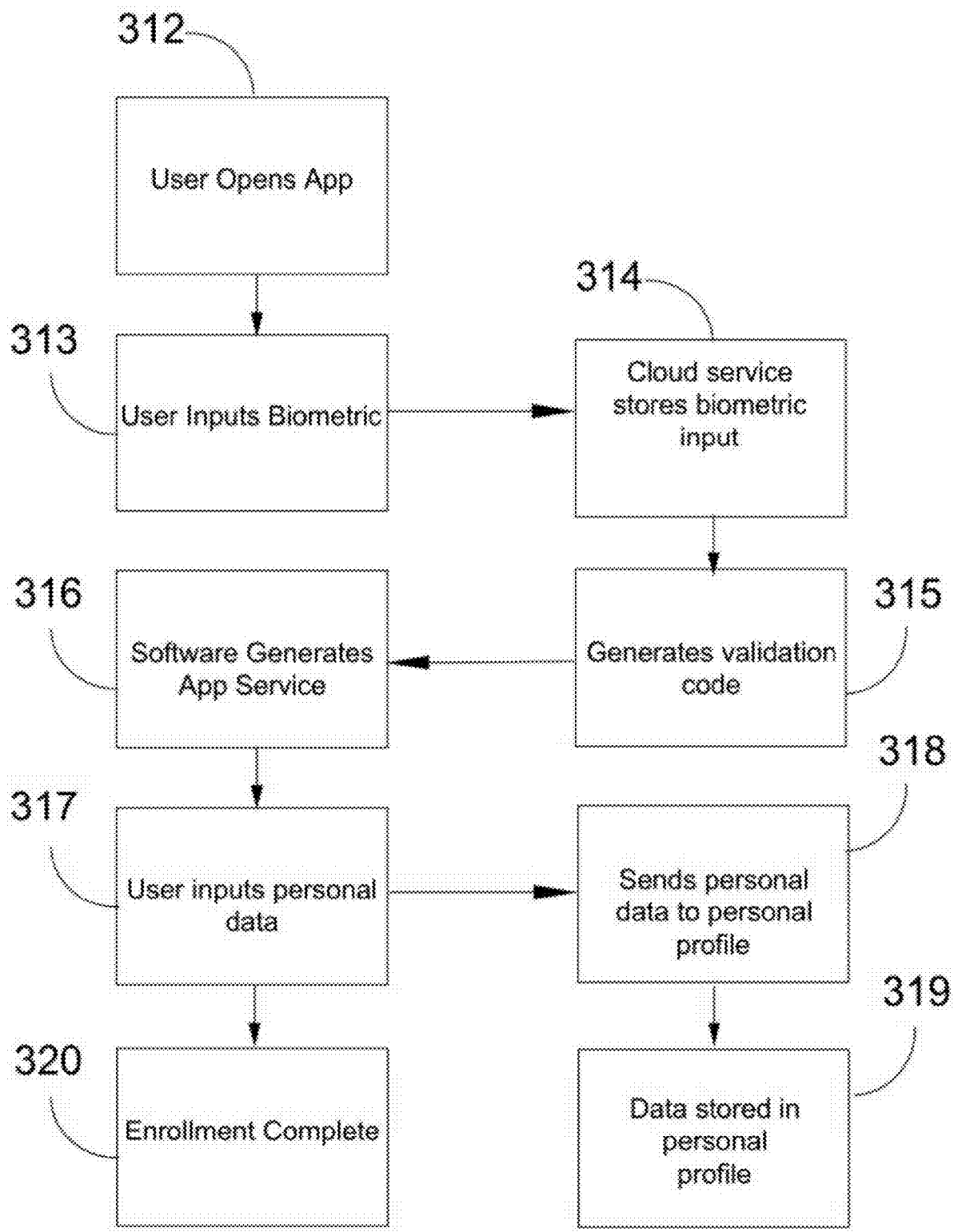
FIG. 25-27 illustrate details of the method of FIG. 24.

Enrollment procedure 310 of inventive method 210, described in FIG. 25, begins at step 312 where user accesses the inventive software, for example via internet on a smartphone optionally operating Android, iOS, Windows Phone, or other mobile operating system, a personal home computer, or an internet-capable read/display device for multiplex codes. Upon opening the software, prior to full launch of the software, the user enters a biometric such as thumbprint, iris scan, retinal scan, or facial recognition scan, or optionally multiple biometrics 313. The software converts the biometric data into a token or some other form of transmittable data and transmits it to a cloud or other server 314.

Once the biometric token is stored on the server, the server generates a validation code and transmits it to the software 315, which unlocks the remaining software features 316. The user manually enters personal information, including but not limited to name, personal identification numbers, address, phone number, and other identifying information and, optionally, other biometrics not entered in previous steps 317. The software transmits all entered personal information and biometrics to the server 318, which securely stores all data associated with the user in a personal profile 319. Once data are transmitted and stored, enrollment procedure 310 is complete 320.

Figure 26:
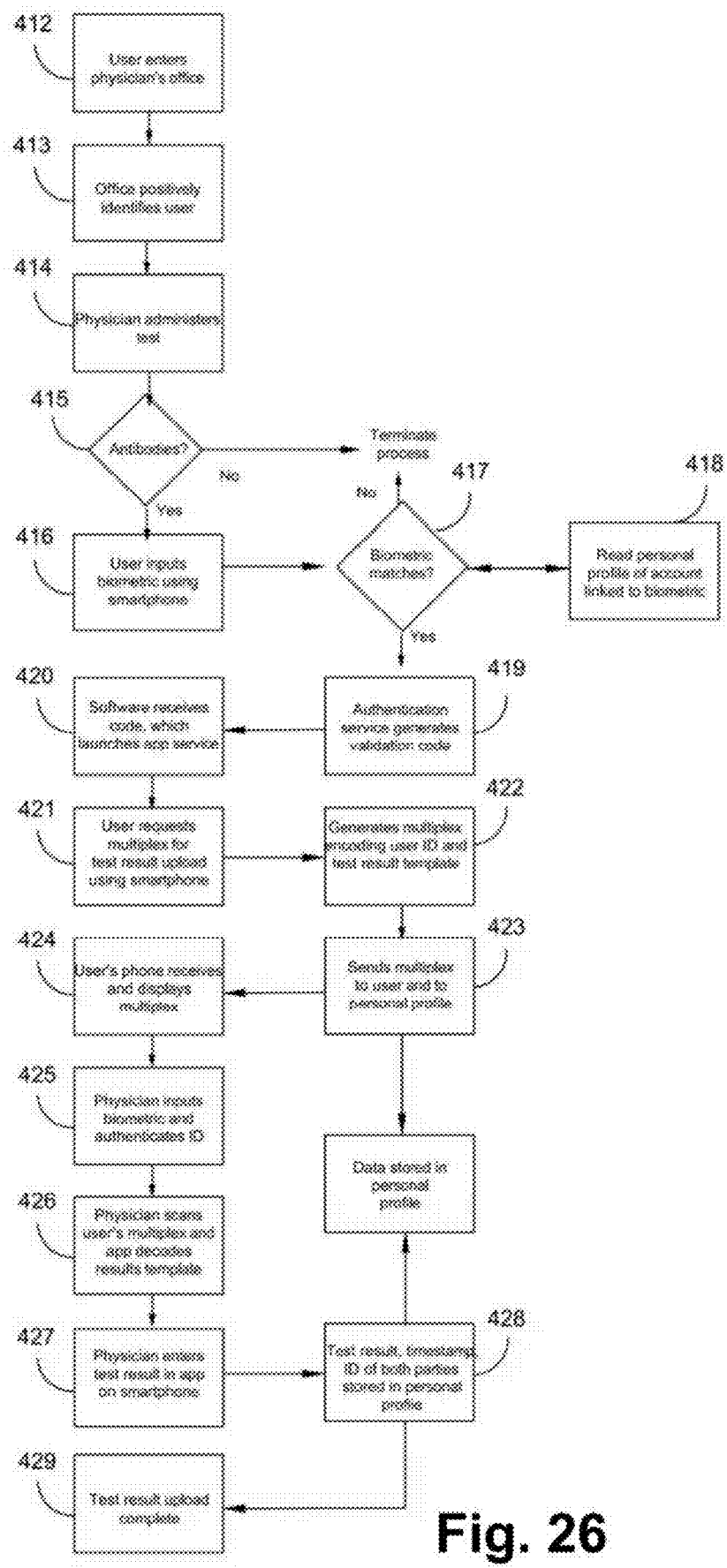

Certification procedure 410 of inventive method 210, described in FIG. 26, begins at step 412 where user presents at a site capable of certifying user's personal information, such as medical information, financial information, personal history, court records, or other sensitive personal information. In an exemplary embodiment, the user presents at a physician's office. The office confirms the user's identity by its typical means of identifying patients 413.

The user then receives a diagnostic medical test or procedure 414, such as that to detect COVID-19 antibodies or other antibody titer, vaccinations, respiratory function tests, or other desired medical examination. If the test returns a negative result, the operation is terminated, but if the result is positive 415 the user inputs a biometric of a type previously stored during enrollment into the user software 416.

The entered biometric is converted into a token, which is checked against the previously stored token by the server's user authentication service 417-418. If the token is not recognized, the operation is terminated. If the token is recognized, the user authentication service generates a validation code and transmits it to the user software 419. Upon receipt of the validation code, the software completes its launch 420.

The user then uses the application to request a multiplex code containing the desired personal information to be encoded along with the desired transaction, in this case a medical diagnostic test 421. The server then generates a multiplex code including personal identity information and a template for medical diagnostic test results and, optionally, an expiration time 422. This multiplex code is temporarily stored in the user's personal profile and is also transmitted to the user software 423.

Upon receipt, the software optically displays the multiplex code 424 or wirelessly transmits an equivalent security device. The physician then inputs a biometric on the physician's smartphone or other reading device 425, triggering the same authorization steps for the physician's identity and launch of the application, as in 416-420 for the user.

The physician then scans the user's multiplex code with a reading device such as a smartphone, multiplex code reader, or other reading device 426, and the multiplex code is decoded by the application software 427. The physician then adds the test results to the template included in the decoded multiplex code, and the test results, authenticated identities of the user and the physician, a timestamp, and the location, and optionally any other information, are transmitted to and stored in the user's personal profile 428. At this point, the certification process is complete 429.

Figure 27:
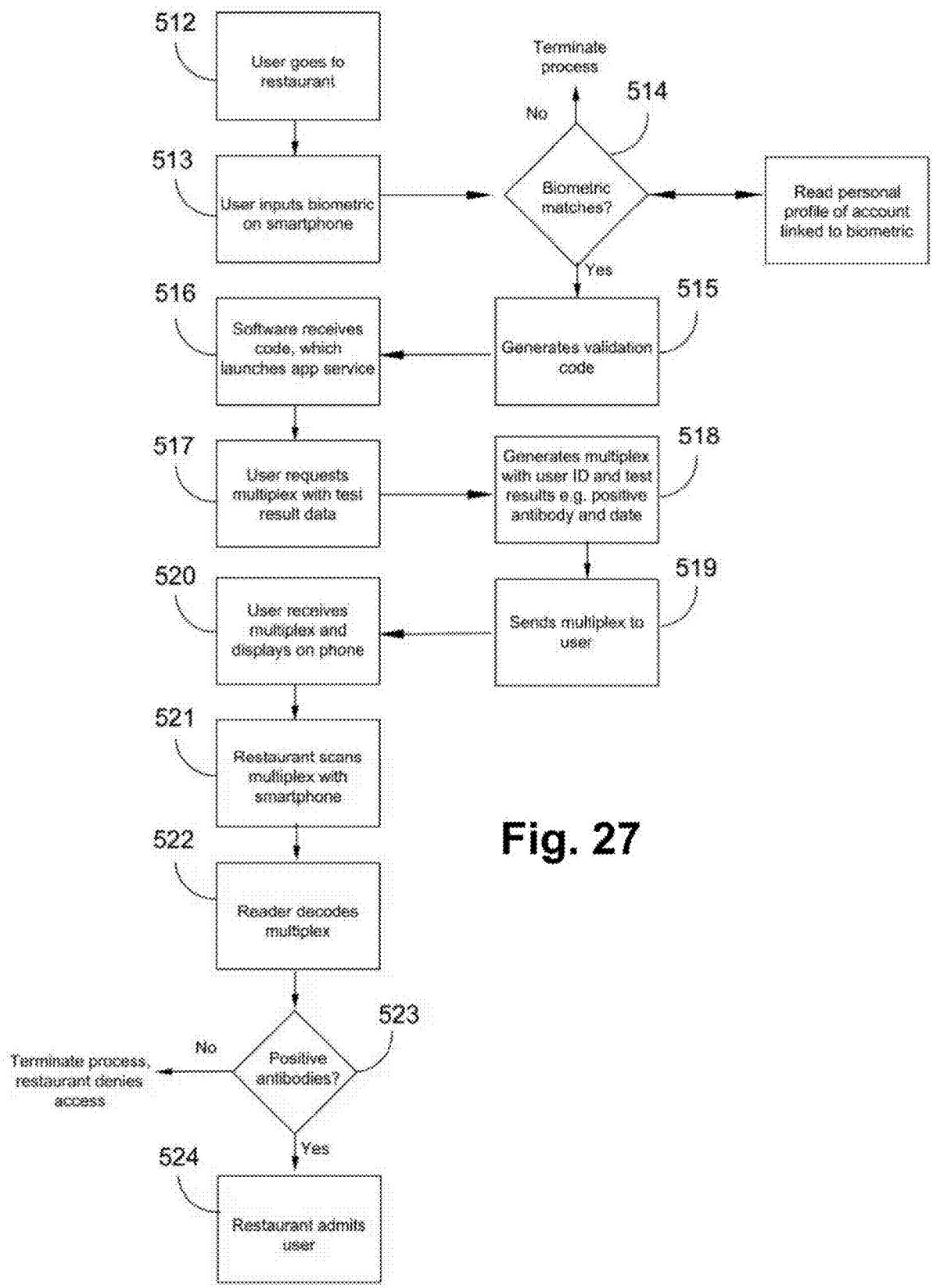

Commercial procedure 510 of inventive method 210, described in FIG. 27, begins at step 512 where the user presents at an establishment requiring certain certified information about the user prior to allowing access, such as a restaurant, retailer, sporting venue, or other physical establishment. In the exemplary embodiment, a user with test results uploaded to the personal profile as described above presents at a restaurant requiring positive COVID-19 antibody test results 512. The user then inputs a biometric of a type previously stored during enrollment into the software 513. The entered biometric is converted into a token, which is checked against the previously stored token by the server user authentication service 514.

If the token is not recognized, the operation is terminated. If the token is recognized, the user authentication service generates a validation code and transmits it to the user software at step 515. Upon receipt of the validation code, the application completes its launch at step 516.

The user then uses the software to request a multiplex code containing the desired personal information to be encoded along with the desired transaction, in this case a verification of positive antibody test results 517. The server then generates a multiplex code including personal identity information and verification of positive antibody test results 518.

This multiplex code is transmitted to the user software 519, and the application optically or wirelessly displays it 520. The restaurant then scans the user's multiplex code with a smartphone, multiplex code reader, or other reading device 521, and the multiplex code is decoded by the software 522. If the decoded message confirms the user's positive antibody test results 523, the user is admitted to the restaurant by an employee, a mechanized locking system connected to the multiplex reader, or some other means 524.

Figure 28:
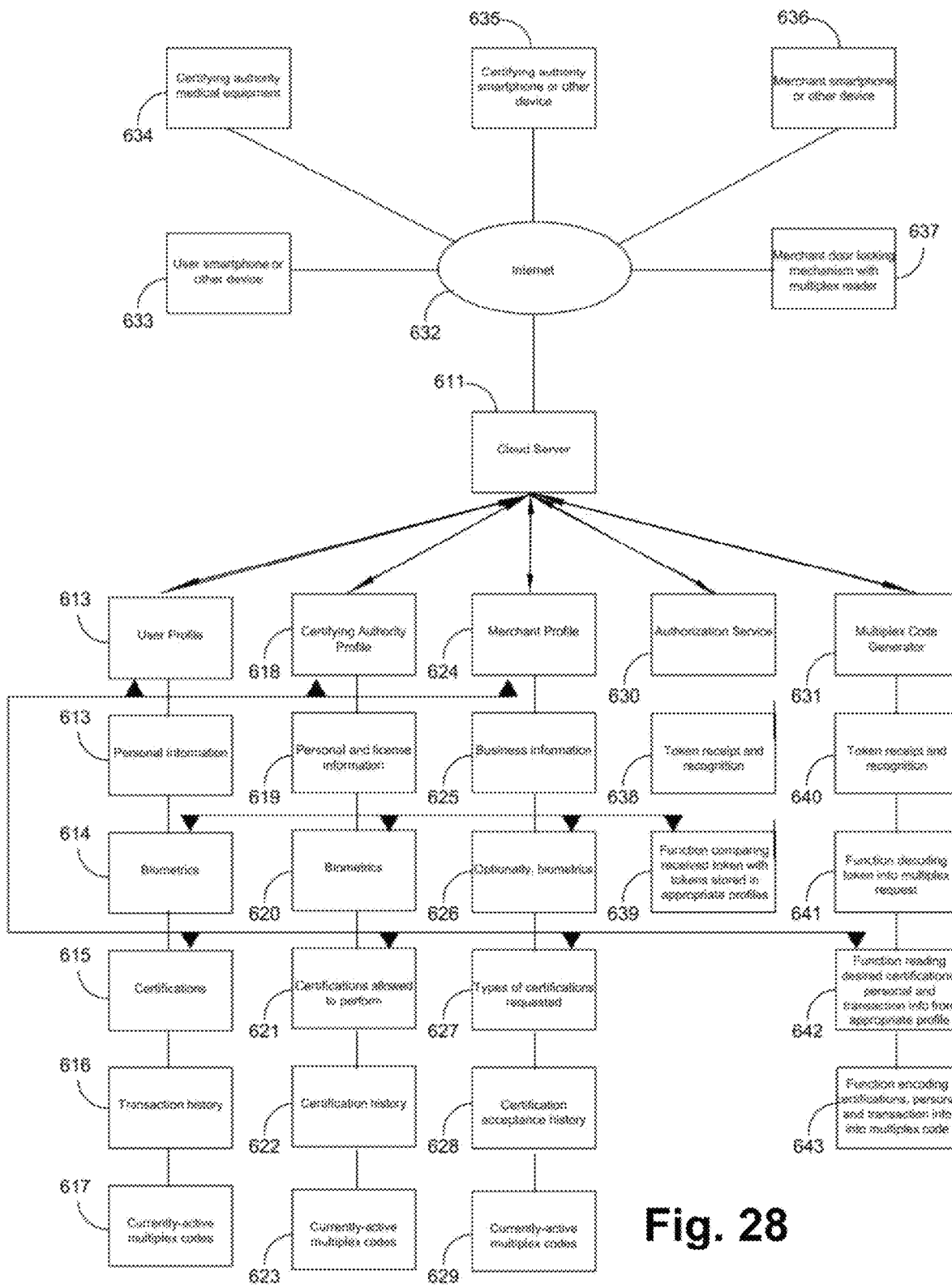
FIG. 28 illustrates hardware for implementing the present invention.

The operation of the system hardware 510 on which the inventive method 210 is implemented, is described with reference to FIG. 28. Cloud server 612 is central to the carrying out of the method steps 310-510, as described above. The server contains non-volatile physical databases, such as hard drives, solid-state memory, solid state drives or the like containing information representing profiles for different types of users, for example consumer users 613, certifying authorities 618 such as physicians, and merchant users 624.

In accordance with the invention, a consumer user profile contains information including personal information 613 such as name, social security number, driver's license number, birthdate, address, phone number, or other identifying information, biometrics scanned during the enrollment procedure 614 (such as a face, fingerprint, and image of the eye, and so forth), any certifications uploaded by certifying authorities such as physicians 615, history of any transactions the user has conducted through the server 616, and any currently-active multiplex codes 617.

In accordance with the invention it is contemplated that the multiplex codes will, optionally, be generated on the fly with respect to a particular authentication transaction and need to be verified by the intended party within a limited period of time.

A certifying authority profile (for example the profile of the doctor who performs test to determine the presence of a particular antibody indicative of, for example, prior infection with a particular pathogen) contains information relating to the certifying authority. Such certifying authorities may be enrolled, much as consumer users are enrolled, and all transactions carried out by the certifying authority (for example doctor or nurse practitioner) would be authenticated using the biometric input by the certifying authority during enrollment. Such information may, and is expected to, include personal information 619 such as name, professional license information, social security number, driver's license number, birthdate, address, phone number, or other identifying information, biometrics scanned during the enrollment procedure 620, listing of any certifications that the certifying authority is authorized to perform 621, such as antibody testing results as in the exemplary embodiment, history of any certifications performed through the server 622, and any currently-active multiplex codes 623.

A merchant profile contains business information 625 such as address, phone number, or other identifying information, a listing of the types of certifications requested of users by the merchant 627, history of any certification accepted 628, any currently-active multiplex codes, and, optionally, employee biometrics for applications requiring identity authentication on the merchant's end 626.

The cloud server containing the user profiles and associated information is connected to the internet 632, which connects the server with users, as described in procedure steps 310-510. The cloud server may be accessed via a consumer user's 633, certifying authority's 635, or merchant's 636 smartphone, tablet, or other multiplex code read/display device. Alternatively, the cloud server may be accessed via any internet-connected equipment at the site of the certifying authority 634, such as medical equipment. The cloud server may also be accessed via a merchant's door locking mechanism connected to the internet and capable of reading multiplex code 637.

The cloud server uses the connection between users and user profiles to run several services, most importantly the authorization service 630 and multiplex code generator 631. The cloud server contains an authorization service capable of token receipt and recognition 638. This function is connected to a further service capable of reading user stored biometric information and comparing it with the newly-arrived token 639.

The multiplex code generator also contains a function capable of token receipt and recognition 640. It also contains a function capable of decoding a token into a multiplex code request 641. A further function mads the requested certifications, personal information, and transaction information and collects the requested information from the appropriate user's profile 642. A further function is capable of encoding the collected information into a multiplex code 643.

In accordance with the invention, the processes detailed above may vary, for example, the buyer could provide the multiplex code, as opposed to the same being provided by the seller. The multiplex code may be generated by the smart phone of the consumer user and not in the cloud.

In addition, various functionalities may be provided in accordance with the invention, such as a "buy now" function. In such a scenario, user may scan a multiplex code to authorize the user to automatically purchase product without requiring the user to enter pricing or any further information.

In accordance with the invention a multiplex code can also be used to act as an authentication and transmission system for block chain data. For example, implementation could involve having a user turn on a block chain app, with a multiplex code transmission option. In this scenario a sending user establishes a multiplex code. A receiving user then scans the multiplex code. The receiver decodes the multiplex code to extract the information for further use.

Examples of information include but are not limited to bank notes, crypo-currency, property lien documentation, etc.

In one case, each user can be considered a blockchain node for a specific transaction and the multiplex code scan acts as an authentication mechanism between the two nodes.

In another case, one user may need to pass block chain information to another user, and use a multiplex code to encode the information.

In another case, an institution, such as a bank, can transmit sensitive blockchain information to users and use a multiplex code to transmit it.

Another possible application is ridesharing or for Haier taxi service (e.g., Uber). In such a scenario, the Uber app indicates that the driver has arrived at the pick up location. Both passenger and driver are logged into the Uber app in accordance with the operation of that application.

When the passenger gets into Uber car, the passenger may, optionally, implement a setting on Uber App on his or her phone to verify the identity of the driver. In principle, this can be done ahead of time.

In this example, the request would go to the Uber cloud. The Uber cloud server determines the identity of the driver and sends the passenger and driver information to access a generated multiplex code in accordance with the present invention. The multiplex code in the inventive server then validates the driver. The multiplex code in the cloud then sends a display multiplex code to the driver's phone. The multiplex code is that displayed on driver's phone the multiplex code is used to validate the passenger in a validation procedure implemented on the server of the website operator utilizing the inventive system to perform authentications.

The passenger that scans driver's phone and the multiplex code is read, followed by a decode and validate operation performed on the server of the operator of the inventive system. This last step may just be used to enable Uber to know that the passenger and driver are now connected together in real life for a specific Uber ride. It also lets the passenger know that this is the right driver and the driver knows this is the right passenger.

Stadium concession usage may also be implemented in accordance with the invention. For example, a sports fan may be sitting in his assigned seat. If the fan wants a concession product such as a pretzel or a soda he simply scans a physically fixed multiplex code associated with his seat, insofar as such a code is adhered to every seat in the stadium.

Alternatively, alternatively a fixed multiplex code may be printed on each ticket, and that code can be scanned by the fan attending the game.

Still yet another possibility is for the user to open a multiplex code App and log in with a bio-metric entry. Upon the occurrence, the identity of the fan may be verified by the server associated with the inventive system. Upon the presentation of a scan window in the inventive application, the user may scan his seat or ticket multiplex code.

The scan multiplex code is sent to the server cloud for verification of the multiplex code by the server operated by the operator of the inventive system. The verified information validates any forward transaction from this seat to the App.

In accordance with the invention of the smart phone of the fan is, optionally, given a set of menu options for concessions and options, for example, for enhanced social media using the app. Likewise, the fan may select items to purchase.

After such selection, the fan may make payment with payment information already provided to the app, without having to reenter the same in much the same manner as cloud services such as Instacart, Amazon, and the like.

In accordance with this embodiment of the invention, the stadium would operate its own server which would receive purchasing information and would be furnished by the stadium system in its standard fashion.

However, while the stadium system, for example operating in the cloud, may use its own payment system to execute the payment, alternatively, the operator of the inventive system may implement payment of the transaction. Once the order is paid for, it is processed and items are delivered to the seat.

As described above, the system may be used for medical testing verification usage, and for other medical purposes. For example user could go to a medical professional for a procedure or for medical testing.

The medical professional then performs the desired medical task. Because the medical professional has already set up a multiplex code account with the operator of the inventive system, the medical professional may input the necessary medical information into his multiplex code app (after bio-metrically logging in)

the consumer user then logs into his or her multiplex code account, for example, bio-metrically and either party can initiate a multiplex code transaction. In such a transaction both the user and medical professional are verified.

For example, the medical professional may be given a multiplex code may be scanned by the consumer user, and this scan then links the test to the multiplex code user and is information record.

Likewise, the medical professional can send test samples to a lab for testing, and when the medical facility receives the test results from the test lab, it can input information to a secure website to be accessed by the user.

Likewise, user may go to a restaurant or some commerce or socializing location that has a safe zone, and the restaurant can scan a user's multiplex code, either manually or automatically.

Alternatively, a person at the restaurant then visually review medical information on the user's phone, if that individual at the restaurant determines to admit the user into a safe area that filters users based on medical testing and procedure status, the consumer user may enter that area.

While illustrative embodiments of the invention have been described, it is noted that various modifications will be apparent to those of ordinary skill in the art in view of the above description and drawings. Such modifications are within the scope of the invention which is limited and defined only by the following claims.

What is claimed:

1. A method for authentication applicable, for example, to controlling access to a space at a controlled access venue, wherein the operator of said controlled access venue wishes to knit access to said venue to individuals who have tested non-infectious for a particular highly infectious disease or have received a vaccination against said particular highly infectious disease by qualifying individuals for entry into said venue, comprising:

(a) receiving a set of consumer user identification information from each of a plurality of consumer users and storing said sets of consumer user identification information in a consumer user database, each of said sets of consumer user identification information being associated with an associated one of said plurality of consumer users;

(b) receiving a biometric identifier from each of said plurality of consumer users, each of said biometric identifiers being associated with an associated one of said plurality of consumer users, and storing said biometric identifiers in said consumer user database with associative information associating each biometric identifier with its associated consumer user to form an enrollment record;

(c) verifying the identity of a presented individual at a medical certification authority, by:

(i) receiving presented consumer user identification information from the consumer user whose identity is to be verified;

(ii) acquiring from a consumer user a locally generated biometric identifier of the type stored in said consumer user database directly from the individual whose identity is to be verified, and associating it with said received presented consumer user information to form a presented set of consumer user identification information;

(iii) comparing said presented set of consumer user identification information to the sets of consumer user identification information stored in said consumer user database to determine whether there is a match between consumer user identification information stored in said database and said presented set of consumer user identification information; and (iv) reading the enrollment record associated with said presented individual and accessing medical records to determine whether said presented individual has tested non-infectious for said particular highly infectious disease or otherwise tested as being non-infectious for a particular highly infectious disease, or has received a vaccination against said particular highly infectious disease indicating that the individual is qualified for entry into said venue;

(d) generating a comparison verification signal in response to the determination that the presented set of consumer user identification information and the locally generated biometric identifier match a set of consumer user identification information including its associated biometric identifier and that the individual is qualified for entry into said venue, said comparison verification signal generation, or performing a certification procedure with respect to said presented individual which generates a certification result indicating that the presented individual is non-infectious, and supplementing said enrollment record with such test information and qualifying said individual for entry into said venue;

(e) storing said certification result;

(f) providing to a particular portable communications device associated with the presented consumer user or to the controlled access venue, in response to a request originated from said particular portable communications device of the consumer user an identification signal to be processed at said venue as is a verification that the presented consumer user has been verified as having been verified as eligible for entry into the controlled access venue; and (g) providing said particular consumer user access to said controlled access venue in response to said identification signal to allow access to said presented consumer user.

2. A method as in claim 1, wherein said plurality of sets of consumer user identification information associated with said plurality of consumer users is stored in memory associated with a server operated by a website operator, and wherein said storing is implemented by transmission to said server over the Internet.

3. A method as in claim 2 wherein said biometric identifiers are stored in said memory associated with said server.

4. A method as in claim 3, wherein verification steps (c) (i) through (c) (iv) are performed by said medical certification authority's accessing the server of said website operator over the Internet.

5. A method as in claim 1, wherein said establishment has a publicly displayed and publically accessible coded information device, and said request is generated in response to reading of said coded information device by said particular portable communications device associated with said particular consumer user.

6. A method as in claim 5, wherein said coded information device is a coded graphic which identifies the establishment, and wherein the particular portable communications device associated with the particular consumer user transmits identification information to the server of the website operator, and wherein the server operated by the website operator, in response to the reception of the transmitted identification information associated with the establishment and identification information associated with the particular consumer user, transmits an admission signal to said establishment.

7. A method as in claim 6, wherein the admission signal operates a lock at the door of the establishment to allow entry to the establishment by the particular consumer user.

8. A method as in claim 7, wherein the establishment is an automobile for hire and the lock is an automotive doorlock.

9. A method as in claim 6, wherein the identification information is transmitted to the server over the Internet, causing the server to transmit a code which is optically displayed on said particular communications device, and said code on the phone is scanned at the establishment and unlocks the door to the establishment.

10. Apparatus for controlling access to a venue, comprising:
(a) a consumer user database;
(b) a plurality of input devices for receiving a plurality of sets of consumer user identification information;
(c) a server;
(d) a communications channel coupled to at least one of said input devices to receive said consumer user identification information associated with consumer users and transmit said consumer user information to said server for storage in a consumer user database;
(e) a reader associated with a communications device associated with a particular consumer user for reading a biometric identifier, said biometric identifier being associated with an associated one of said plurality of consumer users, and storing said biometric identifiers in said consumer user database with associative information associating each biometric identifier with its associated consumer user to form an enrollment record;
(f) a non-volatile memory coupled to said server and storing a software program controlling said server to verify the identity of a presented individual by:

(i) acquiring a locally generated biometric identifier of the type stored in said consumer user database directly from the individual whose identity is to be verified;
(ii) comparing said presented set of consumer user identification information to the sets of consumer user identification information stored in said consumer user database to determine whether there is a match between consumer user identification information stored in said database and said presented set of consumer user identification information;
(iii) comparing said locally generated biometric identifier to biometric identifiers stored in said consumer user database to determine whether there is a match between biometric identifiers stored in said consumer user database and said locally generated biometric identifier; and
(iv) accessing a cleared individual database of individual identification information indicating whether individuals are verified as being non-infectious for a contagious disease to determine if said presented individual is non-infectious and generating a comparison verification signal in response to the determination that the presented set of consumer user identification information and the locally generated biometric identifier match a set of consumer user identification information and its associated biometric identifier for an individual that is non-infectious;
(g) in response to an indication that said presented individual is non-infectious, giving the venue an indication that the individual is verified as being non-infectious for the particular contagious disease by sending a verification signal to said venue; and
(h) providing said particular consumer user access to said establishment by operation of a device selected from the group consisting of a lock, a display for displaying a message indicating that the particular consumer user is to be given admission, another mechanical device dividing admission and a physiologically perceptible device for informing a human located at said establishment.

11. A method for limiting exposure to infectious disease and controlling access to a service at a controlled access venue, wherein the operator of said controlled access venue wishes to limit exposure to infectious disease at said venue by limiting access to individuals who have tested non-infectious for a particular highly infectious disease or have received a vaccination against said particular highly infectious, comprising:
(a) receiving a set of consumer user identification information from each of a plurality of consumer users and storing said sets of consumer user identification information in a consumer user database, each of said sets of consumer user identification information being associated with an associated one of said plurality of consumer users;
(b) receiving a biometric identifier from each of said plurality of consumer users, each of said biometric identifiers being associated with an associated one of said plurality of consumer users, and storing said biometric identifiers in said consumer user database with associative information associating each biometric identifier with its associated consumer user to form an enrollment record;
(c) verifying the identity of a presented individual at a medical certification authority, said collecting comprising:

(i) receiving presented consumer user identification information from the consumer user whose identity is to be verified;
(ii) acquiring from a consumer user a locally generated biometric identifier of the type stored in said consumer user database directly from the individual whose identity is to be verified, and associating it with said received consumer information to form a presented set of consumer user identification information;
(iii) comparing said presented set of consumer user identification information to the sets of consumer user identification information stored in said consumer user database to determine whether there is a match between consumer user identification information stored in said database and said presented set of consumer user identification information; and
(iv) reading the enrollment record associated with said presented individual and accessing medical records to determine said presented individual has tested non-infectious for said particular highly infectious disease or otherwise tested as being non-infectious for a particular highly infectious disease, or has received a vaccination against said particular highly infectious disease indicating that the individual is qualified for entry into said venue;
(d) generating a comparison verification signal in response to the determination that the presented set of consumer user identification information and the locally generated biometric identifier match a set of consumer user identification information, including its associated biometric identifier and that the individual is qualified for entry into said venue, said comparison verification signal generation comprising, or performing a certification procedure with respect to said presented individual which generates a certification result, and supplementing said enrollment record with such test information and qualifying said individual for entry into said venue;
(e) storing said certification result;
(f) collecting a biometric from a venue presented consumer at a presentation venue consumer ii) comparing it to the enrollment records for a match, and iii) providing at the presentation venue, in response to a request from a portable communications device associated with the venue presented consumer user or to the controlled access venue, a verification that the venue presented consumer has been verified as having been verified as eligible for entry into the controlled access venue; and
(g) providing said particular consumer user access to said controlled access venue in response to said identification signal to allow access to said presented consumer user.

12. A method as in claim 11, wherein i) said biometric is collected from said venue presented consumer at said presentation venue, which venue presented consumer is requesting food or other service using a portable communications device associated with the venue presented consumer and ii) said portable communications device associated with the venue presented consumer scans a physical element to generate and transmit information.

13. A method for limiting exposure to infectious disease by controlling access to a controlled access venue, wherein the operator of said controlled access venue wishes to limit exposure of persons in the venue to infectious disease by permitting access to the venue to individuals who have tested non-infectious for a particular highly infectious disease or have received a vaccination against said particular highly infectious disease, comprising:
(a) receiving, at a central website operator server, a set of consumer user identification information from each of a plurality of consumer users and storing said sets of consumer user identification information in a consumer user database associated with said server, each of said sets of consumer user identification information being associated with an associated one of said plurality of consumer users;
(b) receiving at a consumer user device a biometric identifier from each of said plurality of consumer users and transmitting said biometric identifiers to said consumer user database associated with said server, each of said biometric identifiers being associated with a respective one of said plurality of consumer users, and storing said biometric identifiers in said consumer user database associated with respective consumer user identification information, whereby said biometric identifiers are each associated with respective associated consumer user to form an enrollment record;
(c) collecting the identity of a presented individual at a medical certification point, said collecting comprising:
(i) receiving presented individual identification information from the presented individual at said medical certification point; and
(ii) creating an authority record associated with said presented individual at an accessible authority database;
(d) performing, at said medical certification point, a certification procedure on said presented individual to generate a certification result indicating whether or not the presented individual is non-infectious for a particular highly infectious disease or has received a vaccination against said particular highly infectious disease;
(e) supplementing said authority record with such certification result;
(f) collecting a biometric from a venue presented consumer at a presentation venue;
(g) comparing said collected biometric to the authority records for a match;
(h) providing, at the presentation venue, a verification signal indicating that the venue presented consumer has been verified as being non-infectious for a particular highly infectious disease or has received a vaccination against said particular highly infectious disease; and
(i) providing said particular venue presented consumer access to said controlled access venue in response to said signal to allow access to said venue presented consumer.

14. A method as in claim 13, wherein said biometric is collected from said venue presented consumer user at said presentation venue who is requesting food or other service using a portable communications device associated with the venue presented consumer user, and said portable communications device associated with the venue presented consumer user scans a physical element to generate and transmit location information.

15. A method as in claim 13, wherein the creating of an authority record associated with said presented individual at an accessible authority database is done with a non-governmental entity.

* * * * *